(12) United States Patent
Gambhir et al.

(10) Patent No.: US 7,524,674 B2
(45) Date of Patent: Apr. 28, 2009

(54) MULTIMODALITY IMAGING OF REPORTER GENE EXPRESSION USING A NOVEL FUSION VECTOR IN LIVING CELLS AND ANIMALS

(75) Inventors: Sanjiv Gambhir, Portola Valley, CA (US); Ray Pritha, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 0 days.

(21) Appl. No.: 10/548,146

(22) PCT Filed: Mar. 8, 2004

(86) PCT No.: PCT/US2004/007154

§ 371 (c)(1),
(2), (4) Date: Aug. 15, 2006

(87) PCT Pub. No.: WO2004/081189

PCT Pub. Date: Sep. 23, 2004

(65) Prior Publication Data

US 2006/0277613 A1    Dec. 7, 2006

(51) Int. Cl.
| | |
|---|---|
| *C12N 15/00* | (2006.01) |
| *C07H 21/04* | (2006.01) |
| *A61K 31/713* | (2006.01) |
| *A61K 38/02* | (2006.01) |
| *C07K 2/00* | (2006.01) |
| *C12N 15/62* | (2006.01) |

(52) U.S. Cl. .......... 435/320.1; 435/69.1; 435/69.7; 536/23.4; 514/44; 424/192.1; 530/350

(58) Field of Classification Search .......... None
See application file for complete search history.

(56) References Cited

U.S. PATENT DOCUMENTS

2006/0223141 A1* 10/2006 Carey et al. .......... 435/69.1

OTHER PUBLICATIONS

Gambhir et al, PNAS 97(6): 2785-2790, 2000.*
Black et al (PNAS 91: 7247-7251, 1994.*
Strathdee et al, Biotechniques 28(2): pp. 210, 212 and 214, 2000.*
Cohen et al, Transgenic Research 7:321-330, 1998.*
Wilson et al, Bioluminescence 14:197-230, 1998, Abstract only.*
Sharma et al, Br. J. Opthalmol. 81(9):785-788, 1997, Abstract only.*
Greer et al, Luminescence 17:43-74, 2002.*
Wang et al, Mol. Genet. Genomics 268:160-168, 2002.*

* cited by examiner

*Primary Examiner*—Q. Janice Li
*Assistant Examiner*—Kevin K. Hill
(74) *Attorney, Agent, or Firm*—Thomas, Kayden, Horstemeyer & Risley, LLP

(57) ABSTRACT

Novel double and triple fusion reporter gene constructs harboring distinct imageable reporter genes are provided, as well as applications for the use of such double and triple fusion constructs in living cells and in living animals using distinct imaging technologies.

16 Claims, 8 Drawing Sheets

MULTIMODALITY IMAGING OF REPORTER GENE EXPRESSION USING A NOVEL FUSION VECTOR IN LIVING CELLS AND ANIMALS

This invention was made with Government support under contract DE-FC03-87ER60615 awarded by the Department of Energy and by contracts CA 086306, CA092865, and CA082214 awarded by the National Institute of Health. The Government has certain rights in this invention.

"This application claims priority to international application PCT/US2004/007154 filed on Mar. 8, 2004, which claims benefit of the U.S. provisional application 60/452,913, filed Mar. 7, 2003, the contents of each are incorporated by reference in their entirety."

BACKGROUND OF THE INVENTION

Repetitive monitoring of reporter gene expression in intact living animals is crucial for many applications, including cell trafficking, gene therapy studies, and transgenic models (Ray, P., et al. (2001) Semin. Nucl. Med. 31, 321-330). Noninvasive, real-time analysis of molecular events in intact living mammals is an active area of current research (See, e.g., Bremer, C. & Weissleder, R. (2001) Acad. Radiol. 8, 15-23). Several imaging technologies and new reporter genes are being studied for noninvasive imaging and quantitation of gene expression in living subjects. Some of the imaging modalities and established reporter genes include single photon emission computed tomography (SPECT) using Herpes Simplex Virus Type I thymidine kinase HSV1-tk, Somatostatin Type 2 receptor, and Sodium/Iodide Symporter as reporter genes. Positron emission tomography (PET) using HSV1-tk and Dopamine Type 2 Receptor as reporter genes, MRI with various reporter genes, and optical imaging approaches with fluorescence and bioluminescent reporter genes have also been studied. A detailed review of reporter gene approaches for use in living subjects can be found in Ray et al., supra.

Noninvasive imaging of reporter gene expression using various imaging modalities is playing an increasingly important role in defining molecular events in the field of cancer biology, cell biology, and gene therapy. It is important to be able to image reporter gene expression in living cells, animals, and humans using a single reporter construct. A single reporter gene would facilitate rapid translation of approaches developed in cells to preclinical models and clinical applications. To date, various methodologies exist that allow the imaging of reporter gene expression in living cells and animals noninvasively and repetitively. Confocal laser microscopy, two-photon laser microscopy, and several other techniques are available for real-time imaging of gene expression at the single cell level using fluorescence (Piston, D. W. Imaging living cells and tissues by two-photon excitation microscopy. Trends Cell Biol., 9: 66-69, 1999; Jakobs, S., et al., EGFP and DsRed expressing cultures of *Escherichia coli* imaged by confocal, two-photon and fluorescence lifetime microscopy. FEBS Lett., 479: 131-135, 2000). For reporter gene imaging in living subjects PET, single photon emission computed tomography, magnetic resonance imaging, and optical imaging are well standardized and are being used extensively in small animal models (Ray, P., et al. Monitoring gene therapy with reporter gene imaging, Semin. Nucl. Med., 31: 312-320, 2001; Wu, J. C., et al. Optical imaging of cardiac reporter gene expression in living rats, Circulation, 105: 1631-1634, 2002; Bhaunik, S., and Gambhir, S. Optical imaging of renilla luciferase reporter gene expression in living mice, Proc. Natl. Acad. Sci. USA, 99: 377-382, 2002) and more recently with PET in humans (Yaghoubi, S. S., et al. PET imaging of FHBG in humans: a tracer for monitoring herpes simplex virus type 1 thymidine kinase suicide gene therapy, J. Nucl. Med., 41: 73P-74P, 2000; Jacobs, A., et al., Positron-emission tomography of vector-mediated gene expression in human gene therapy for gliomas, Lancet, 358: 727-729, 2001). These imaging techniques play important roles in defining critical pathways involved in tumorigenesis, metastasis, and evaluating the efficiency of gene therapy strategies (Vooijs, M., et al., Noninvasive imaging of spontaneous retinoblastoma pathway-dependent tumors in mice, Cancer Res., 62: 1862-1867, 2002; Gambhir, S. S. Molecular Imaging of cancer with positron emission tomography, Nat. Rev. Cancer, 2: 683-693, 2002, Yang, M., et al., Whole-body optical imaging of green fluorescent protein expressing tumors and metastases. Proc. Natl. Acad. Sci. USA, 97: 1206-1211, 2000). Each of these modalities has unique applications, advantages, and limitations that can be complementary to other modalities. A cell-based technique is not useful for whole body in vivo imaging studies, whereas techniques involved in imaging at the tissue or organism level do not have the resolution power to image gene expression at the cellular level. Among the whole body imaging modalities, the radionuclide-based techniques have high sensitivity, good spatial resolution, and are tomographic in nature but are somewhat limited by their higher cost and especially for PET, the need for a cyclotron for production of isotopes for most tracers. In contrast, optical imaging techniques (fluorescence and bioluminescence) represent a low cost and quick alternative for real-time analysis of gene expression in small animal models (Wu, supra; Yang, supra) but are limited by depth penetration and cannot be easily generalized to human applications.

To overcome the shortcomings of each modality, a multimodality approach should be very useful for detecting reporter gene expression. Combining two or more different technologies (e.g., PET with optical) through a unified vector would have the advantage of speed and ease of validating approaches in small animals that in turn can be translated to humans. Such a vector might be achieved by several different approaches. A single reporter gene can be investigated for a single substrate doubly labeled with different signatures such as a radioactive nuclide (suitable for radionuclide imaging) or a nonradioactive paramagnetic/bioluminescent/fluorescent molecule (suitable for magnetic resonance or optical imaging) and thus can be imaged by different imaging modalities. However, development of such substrates is often difficult because of the complex chemical nature of the biomolecules and limitations on required pharmacokinetics in vivo.

What is needed, therefore, is a single vector harboring two or more different reporter genes imaged by two or more different techniques (e.g., one radionuclide and one optical). Coexpression of multiple genes is generally achieved by using multiple promoters by insertion of an internal ribosomal entry site or by fusing the two (or more) genes into a single translational cassette (Ray, P., et al., supra, Semin. Nucl. Med., 31: 312-320). Our laboratory has successfully used tk (HSV1-sr39 thymidine kinase, an improved PET reporter gene over the wild-type HSV1-tk when using the guanosine analogues as tracer) and rl (renilla luciferase, a bioluminescence optical reporter gene) as separate imaging tools for studying the location, magnitude, and time variation of reporter gene expression in living subjects (Bhaumik, S., supra; Gambhir, S. S., et al., A mutant herpes simplex virus type 1 thymidine kinase reporter gene shows improved sensitivity for imaging reporter gene expression with positron emission tomography, Proc. Natl. Acad. Sci. USA, 97: 2785-

2790, 2000; Yu, Y., et al., Quantification of target gene expression by imaging reporter gene expression in living animals, Nat. Med., 6: 933-937, 2000).

The present inventors have now constructed and validated a novel tk and rl fusion protein imaged by microPET and bioluminescent optical CCD imaging modalities in tumor xenograft-bearing living mice. The present inventors have further constructed and validated triple fusion reporter constructs, including one combining a synthetic renilla luciferase (hrl), a red fluorescence protein (rfp or DsRed2) and a truncated version of sr39tk (ttk) that can be used to image in a single live cell using a fluorescence microscope and in living mice with both an optical cooled charged couple device (CCD) camera and microPET.

DETAILED DESCRIPTION OF THE INVENTION

Figure 1:
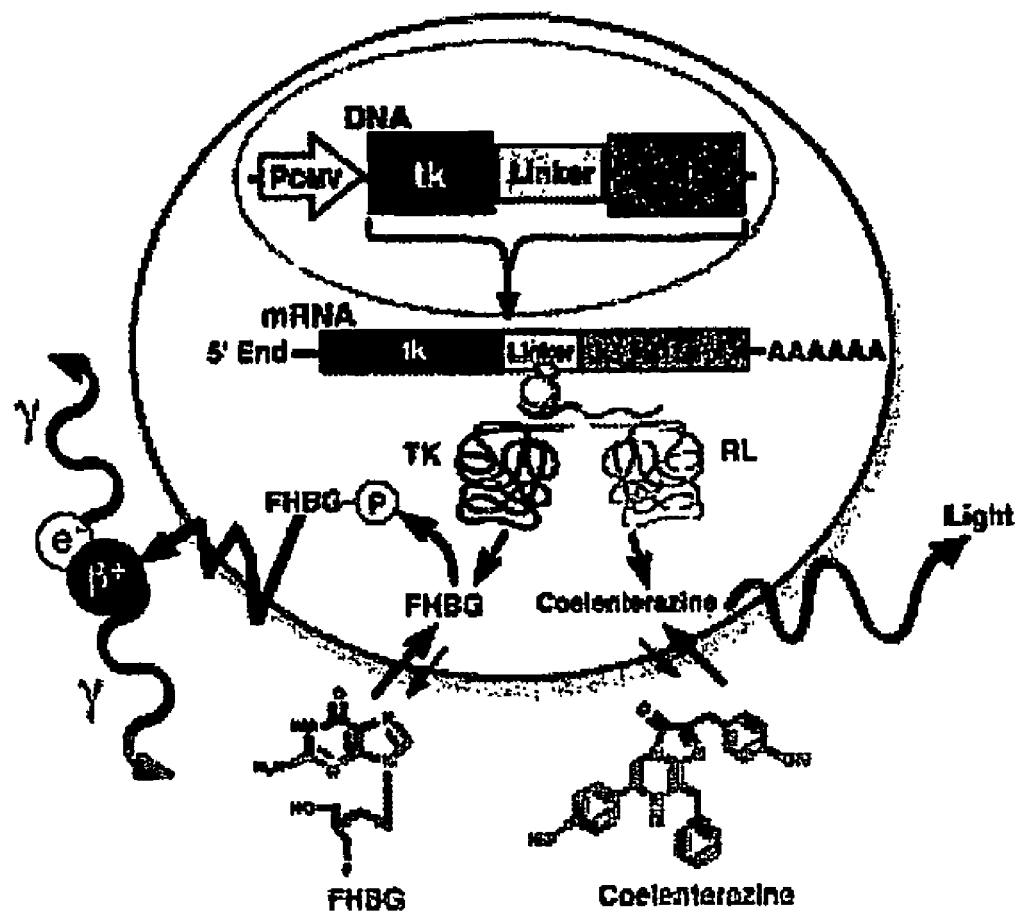
FIG. 1. Measuring reporter gene expression using two different imaging modalities when two reporter genes are simultaneously expressed from a fusion vector. tk, a PET reporter gene is fused with rl (renilla luciferase), an optical bioluminescence reporter gene with the help of a polynucleotide coding for a short 20 a.a. long spacer and expression is driven by a CMV promoter. Transcription of this fusion vector yields a single mRNA, and subsequent translation leads to a single polypeptide that is capable of retaining partial if not full activities of the two proteins fused. Noninvasive, quantitative, and repeated imaging of the location and magnitude of the both reporter gene expression either by trapping of a PET reporter probe (e.g., FHBG phosphorylated by TK enzyme) or by catalysis of an optical reporter probe (e.g., production of light through RL-coelenterazine reaction) can be imaged by both microPET and optical CCD camera in living subjects, respectively.

The abbreviations used herein are: PET, positron emission tomography; tk/TK, HSV1-sr39 thymidine kinase gene/protein; rl/RL, renilla luciferase gene/protein; β-gal/β-GAL, β-galactosidase gene/protein; CCD, cooled charge-coupled device; FHBG, 9-(4-[$^{18}$F]fluoro-3-hydroxymethylbutyl)guanine; FDG, 2-[$^{18}$F]fluoro-2-deoxyglucose; N2a neuro 2a; FBS, fetal bovine serum; PCV, penciclovir; CMV, cytomegalovirus; ROI, regions of interest; % ID/g, percentage of injected dose/gram; p/sec/cm$^2$/sr, photons/second/cm$^2$/steradian; gfp, green fluorescence protein; fl/FL, firefly luciferase gene/protein; rfp, red fluorescent protein; FACS, fluorescence-activated cell sorting.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

One aspect of the present invention relates to a triple fusion vector harboring a PET, a bioluminescence and a fluorescence reporter gene that is imageable in living cells using a fluorescence microscope as well as in living mice using a Positron Emission Tomographic scanner, a charge couple device (CCD) camera for both fluorescence and bioluminescence imaging. This single reporter vector can be used to follow cellular and molecular processes in living cells and subsequently in living subjects. By having a single reporter one can easily move between cells, small animal models and humans with great ease as compared to using separate reporters for each application. This is the first report of a multimodality reporter vector carrying three genes that can noninvasively, repeatedly and quantitatively image gene expression in living cells and in small living animals.

Another aspect of the present invention relates to a double fusion reporter construct carrying a PET reporter and a bioluminescent reporter gene, which has been made and tested in various cell culture and in living mice by tumor xenograft model.

In the practice of the present invention, a cell line or gene therapy vector or transgenic animal is marked with this reporter vector. Then, utilizing the three different imaging modalities (PET, Bioluminescence and Fluorescence) and appropriate tracer/substrate or imaging conditions, gene expression is imaged in a single living cell as well as in living animals. The method can be used for detecting expression of reporter genes in intact organisms, as well as in tissues and organs being maintained in culture or in tissue slices or other ex vivo or in vitro situations.

In one embodiment of the present invention, the triple fusion vector, constructed using standard techniques, harbors HSV1-sr39 thymidine kinase (a PET reporter gene), renilla luciferase (a bioluminescent gene) and red fluorescence protein (a fluorescence gene). The vector may also be constructed with firefly luciferase and wild type HSV1 thymidine kinase genes. It is unique in that it can be used to track the cellular events in a living cell by using a standard fluorescence microscope, which then can be translated in living subjects using the PET, bioluminescence and Fluorescence in vivo imaging modalities. This vector has the potential to translate approaches developed at the cellular level to pre-clinical models to clinical applications and has been tested in N2a (a murine neuroglial cell line) and 293T (human embryonic kidney cell line) by transient transfection and is currently under validation in other cell lines. Clones of N2a cells stably expressing this vector are also being isolated.

Reporter genes suitable for practice of the present invention include, but are not limited to, genes encoding polypeptides having imageable properties; that is, polypeptides that may be detected by means such as MRI, PET, and visualization of bioluminescence or fluorescence, as well as other means known in the art.

Polypeptides detectable by PET include, but are not limited to, wild type and mutant thymidine kinase as described in the references cited herein (see, e.g., Yaghoubi, S. S., et al., J. Nucl. Med., 41: 73P-74P, 2000; Jacobs, A., et al., Lancet, 358: 727-729, 2001).

Bioluminescent polypeptides include, but are not limited to, renilla luciferase and firefly luciferase. The enzyme renilla luciferase (RL), purified from sea pansy (Renilla reniformis), is a bioluminescent compound that displays blue-green bioluminescence upon mechanical stimulation. It is widely distributed among coelenterates, fishes, squids, and shrimps (J. W. Hastings, (1996) Gene 173, 5-11). It has been cloned and sequenced by Lorenz et al. (1991) Proc. Natl. Acad. Sci. USA 88, 4438-4442, and used as marker of gene expression in bacteria, yeast, plant, and mammalian cells (W. W. Lorenz et al., (1996) J. Biolumin. Chemilumin. 11, 31-37). The enzyme RL catalyzes coelenterazine oxidation leading to bioluminescence.

Coelenterazine consists of an imidazolopyrazine structure, {2-(p-hydroxybenzyl)-6-(p-hydroxyphenyl)-8-benzylimidazo [1,2-a]pyrazin-3-(7H)-one} that releases blue light across a broad range, peaking at 480 nm upon oxidation by RL in vitro (J. C. Matthews et al., (1977) Biochemistry 16, 5217-5220).

Another well-characterized bioluminescent enzyme is known as firefly luciferase ("FL"), because it was isolated from the lightning bug or the firefly. Like RL, FL will also produce light in the presence of its substrate, which in this case is d-luciferin. FL has been used in live animal systems, and the resulting light production imaged. See, for example, U.S. Pat. Nos. 5,650,135 and 6,217,847, the entire contents of which are incorporated by reference herein. Firefly luciferase is a 61-kDa single-subunit protein that catalyzes D-luciferin to produce oxyluciferin in the presence of oxygen, cofactors, $Mg^{2+}$, and ATP to yield green light at 562 nm. The two luciferases (RL and FL) and the two substrates coelenterazine and D-luciferin are structurally unrelated.

Other examples of bioluminescent polypeptides are known in the art. One of skill in the art will appreciate that, depending on the bioluminescent polypeptide incorporated into the fusion vector, a suitable substrate may be administered to the cell(s) or animal containing the vector; e.g., coelenterazine for RL, D-luciferin for FL, and the like.

Examples of fluorescent polypeptides suitable for use in the present invention include, but are not limited to, red fluorescing protein and green fluorescing protein as described in the references cited herein (see, e.g., Yang, M., et al., Proc. Natl. Acad. Sci. USA, 97: 1206-1211, 2000; Jakobs, S., et al., FEBS Lett., 479: 131-135, 2000).

It should be noted that incorporating fluorescent reporter genes into the fusion vectors of the present invention allows for cell sorting using FACS (Fluorescent activated cell sorting). This provides a high-throughput method for sorting cells expressing the fusion vector (and thus expressing the other marker genes present in the fusion vector).

In practice of the present invention, nucleic acid sequences encoding imageable polypeptides are inserted into an expression vector in frame and operably linked to an expression control sequence, so that expression of nucleic acid sequences produces a fused polypeptide comprising two or more imageable polypeptides.

Expression vectors suitable for practice of the present invention are well known in the art and depend, in part, on the cell type in which expression will be monitored. Examples of suitable vector include, but are not limited to pCDNA3.1 and R-Luc N fusion vector (Biosignal Packard, Canada). Others will be apparent to those of skill in the art.

The DNA sequences in the expression vector are operatively linked to an appropriate expression control sequence(s) (promoter) to direct mRNA synthesis. As representative examples of such promoters, there may be mentioned: LTR or SV40 promoter, the E. coli. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression, such as enhancer sequences. Where expression of a particular gene is of interest, expression control sequences for that gene of interest may be incorporated into the expression vector, as will be appreciated by the skilled artisan.

Nucleic acid sequences for several suitable reporter polypeptides are well known in the art and are generally commercially available, as indicated herein and in the references cited herein.

Techniques for inserting nucleic acid sequences into expression vectors, such that nucleic acid sequences are operably linked to expression control sequences and are in frame, are widely known in the art. See, e.g., Sambrook, J., Fritsch, E. and Maniatis, T., Molecular Cloning: A Laboratory Approach, Second Edition (1989; Cold Springs Harbor Laboratory Press).

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Double Fusion Reporter

Introduction

Noninvasive imaging of reporter gene expression using various imaging modalities is playing an increasingly important role in defining molecular events in the field of cancer biology, cell biology, and gene therapy.

In this study, a novel reporter vector was constructed encoding a fusion protein comprised of a mutant herpes simplex virus type 1 thymidine kinase (HSV1-sr39tk) (tk), a positron emission tomography (PET) reporter gene, and renilla luciferase (rl), a bioluminescence optical reporter gene joined by a 20 amino acid long spacer sequence. We validated the activity of the two enzymes encoded by the fusion protein (tk20rl) in cell culture. Then, tumors stably expressing the tk20rl fusion gene were imaged both by microPET and optically using a cooled charge coupled device camera in xenograft-bearing living mice. Using a single fusion reporter (PET/optical) gene should accelerate the validation of reporter gene approaches developed in cell culture for translation into preclinical and clinical models. See FIG. 1 for an overview of this approach.

Materials and Methods.

Chemicals. FDG was synthesized at University of California at Los Angeles as described previously (Hamacher, K., Coenen, H. H., and Stocklin, G. Efficient stereospecific synthesis of no-carrier-added 2[$^{18}$F]-fluoro-2-deoxy-D-glucose using amino polyether supported nucleophilic substitution. J. Nucl. Med., 27: 235-238, 1986). 8-$^3$H-Penciclovir was obtained from Moravek Biochemicals (Brea, Calif.). FHBG (9-(4-[$^{18}$F]fluoro-3-hydroxymethylbutyl) guanine) was also synthesized at University of California at Los Angeles as detailed previously (Yaghoubi, S. S., Goldman, R., Barrio, J. R., Namavari, M., Iyer, M., Satyamurthy, N., Herschman, H. R., Phelps, M. E., and Gambhir, S. S. PET imaging of FHBG in humans: a tracer for monitoring herpes simplex virus type 1 thymidine kinase suicide gene therapy. J. Nucl. Med., 41: 73P-74P, 2000). Coelenterazine was purchased from Biotium, Inc. (Hayward, Calif.). The polyclonal anti-TK antibody was a kind gift of Dr. M. Black (Washington State University, Pullman, Wash.), and the monoclonal anti-RL antibody was purchased from Chemicon International (Temecula, Calif.).

Construction of tk-rl Fusion Gene. PCR amplification and standard cloning techniques were used to insert the tk gene from plasmid pCDNA 3.1, HSV1-sr39tk (Yu, Y., Annala, A. J., Barrio, J. R., Toyokuni, T., Satyamurthy, N., Namavari, M., Cherry, S. R., Phelps, M. E., Herschman, H. R., and Gambhir, S. S. Quantification of target gene expression by imaging reporter gene expression in living animals. Nat. Med., 6: 933-937, 2000) in frame with the rl gene into the R-Luc N fusion vectors (Biosignal Packard, Canada). For PCR amplification, three different 3' end primers:

5'-GAGCCTCGAGGTTAGCCTCCCCCAT-3' (SEQ ID NO: 1);

5'-GAGCGAATTCGTTAGCCTCCCCCAT-3' (SEQ ID NO: 2); and

5'-GAGCAAGCTTGTTAGCCTCCCCCAT-3' (SEQ ID NO: 3) were used along with the same 5' end primer:

5'-GCAGCTAGCCGCCACCATGGCTTCGTACCCC-3' (SEQ ID NO: 4) to eliminate the stop codon of the tk gene and introduce different restriction sites. Cloning of these thee different PCR products of tlc gene into three subtypes of R-Luc N fusion vector (N1, N2, and N3 that differ from each other by 1 or 2 bases in their multicloning sites to provide alternate reading frames) generated spacers differing in length, sequence, and composition.

Cell Lines, Transfection Procedures, and Stable Clone Isolation. C6 rat glioma cells (obtained from Dr. M. Black), N2a neuronal cell lines (obtained from Dr. Vincent Mauro, Scripps Research Institute, La Jolla, Calif.), and 293T human embryonic kidney cells (American Type Culture Collection, Manassas, Va.) were used. The C6 cells were cultured in high glucose, deficient minimal Eagle's medium supplemented with 5% FBS and 1% penicillin (100 µg/ml), streptomycin (292 µg/ml), glutamine (100 mM), and histidinol (27 µg/ml) by volume. The N2a cells were cultured in high glucose DMEM supplemented with 10% FBS and 1% penicillin (100 µg/ml), streptomycin (292 µg/ml), and 293T cells were grown in MEM supplemented with 10% FBS and 1% penicillin/streptomycin solution. All transient and stable transfections were carried out using the Qiagen Superfect transfection reagent (Qiagen, Valencia, Calif.) following the protocol recommended by the manufacturer. The N2a stable cell lines carrying the fusion gene construct were selected with 200 µg/ml of G418. The clones were initially screened for renilla luciferase activity using a CCD camera (Bhaumik, S., and Gambhir, S. Optical imaging of renilla luciferase reporter gene expression in living mice. Proc. Natl. Acad. Sci. USA, 99: 377-382, 2002) and then assayed for thymidine kinase activity (Gambhir, S. S., Barrio, J. R., Phelps, M. E., Iyer, M., Namavari, M., Satyamurthy, N., Wu, L., Green, L. A., Bauer, E., MacLaren, D. C., Nguyen, K., Berk, A. J., Cherry, S. R., and Herschman, H. R. Imaging adenoviral-directed reporter gene expression in living animals with positron emission tomography. Proc. Natl. Acad. Sci. USA, 96: 2333-2338, 1999).

TK, RL, and β-Gal Activity. Thymidine kinase activity assays were performed as previously described (Gambhir, S. S., supra, Proc. Natl. Acad. Sci. USA, 96: 2333-2338), and β-gal and renilla luciferase assays were done using the β-Gal enzyme assay system and Dual-Luciferase Reporter Assay System from Promega (Madison, Wis.), respectively.

Western Blot Analysis. The expression of TK and RL were evaluated by Western blotting with a rabbit polyclonal anti-TK antiserum and a mouse monoclonal antirenilla antibody using cell lysates prepared from 293T cells transfected with tk20rl, HSV1-sr39tk, or rl plasmids (Gambhir, S. S., Bauer, E., Black, M. E., Liang, Q., Kokoris, M. S., Barrio, J. R., Iyer, M., Namavari, M., Phelps, M. E., and Herschman, H. R. A mutant herpes simplex virus type 1 thymidine kinase reporter gene shows improved sensitivity for imaging reporter gene expression with positron emission tomography. Proc. Natl. Acad. Sci. USA, 97: 2785-2790, 2000). A semiquantitative analysis of the Western blot was performed using the MacBAS V2.4 software (Fuji Base 5000, Tokyo, Japan).

MicroPET Imaging of Mice. Animal care and euthanasia were performed with the approval of the University of California Animal Research Committee. Twelve- to 14-week old male nude mice (nu/nu) were injected s.c. with ~2×10$^6$ of N2a cells stably expressing the tk20rl fusion and control nonexpressing N2a cells, and after 8-10 days, tumor-bearing mice were scanned in microPET as described earlier (Gambhir, S. S., supra, Proc. Natl. Acad. Sci. USA, 97: 2785-2790). The microPET images were reconstructed by using three-dimensional filtered back projection and an iterative maximum a posteriori algorithm (Qi, J., Leahy, R. M., Cherry, S. R., Chatziioannou, A., and Farquhar, T. H. High resolution 3D Bayesian image reconstruction using the microPET small-animal scanner. Phys. Med. Biol., 43: 1001-1013, 1998). ROI were drawn over the tumor area The ROI counts were converted to the % ID/g tumor using filtered back projection as previously described (Gambhir, S. S., supra, Proc. Natl. Acad. Sci. USA, 97: 2785-2790), and images shown were reconstructed with maximum a posteriori algorithm.

Optical Imaging of Renilla Luciferase Expression in Vivo. For in vivo optical imaging, mice implanted with stably expressing tk20rl fusion N2a, and control N2a cells were anesthetized and each mouse was then injected with 10 µl of coelenterazine (stock solution, 2 µg/µl in methanol) diluted in 90 µl of PBS (pH 7) via tail vein. Each animal was then placed supine in a light tight chamber, and whole body images were obtained and quantified as described previously (Bhaumik, S., and Gambhir, S., supra, Proc. Natl. Acad. Sci. USA, 99: 377-382).

Results

A HSV1-sr39 Thymidine Kinase PET and Renilla Luciferase Bioluminescence Reporter Gene Fusion Vector Bearing the Coding Sequence for a 20 a.a. Long Spacer Maintains the Highest TK and RL Activity in Three Different Cell Lines. We first constructed a fusion gene vector carrying tk and rl reporter genes using the spacer lengths. The PCR-amplified tk gene fragments from the pCDNA3.1-HSV1-sr39tk plasmid (Yu, Y., supra, Nat. Med., 6: 933-937) were cloned in frame into R-Luc-N fusion vectors to generate a fusion gene construct under the CMV promoter. PCR amplification of tk gene using three different 3' end primers and subsequent cloning of these amplified fragments generated three tk-rl fusion constructs bearing spacers with length and sequence as indicated:

tk20rl (NSHASAGYQACGTAGPGSTG) (SEQ ID NO: 5);

tk18rl (SRVCRISSLRYRGPGITG) (SEQ ID NO: 6); and tk10rl (AVPRARDPTG) (SEQ ID NO: 7).

Plasmid DNA prepared from four to five clones for each spacer type were transiently transfected in 293T cells and assayed for TK and RL activity. The plasmid clones exhibiting the highest TK and RL activities were selected for additional studies (data not shown). Each of the three tk-rl fusion constructs were then subsequently cloned in pCDNA3.1 (+) backbone to directly compare results of each fusion with the pCDNA3.1-HSV1-sr39tk and pCDNA3.1-rl [rl was also cloned in pCDNA3.1 (+) from the R-Luc-N fusion vector], the positive control plasmids.

Figure 2:
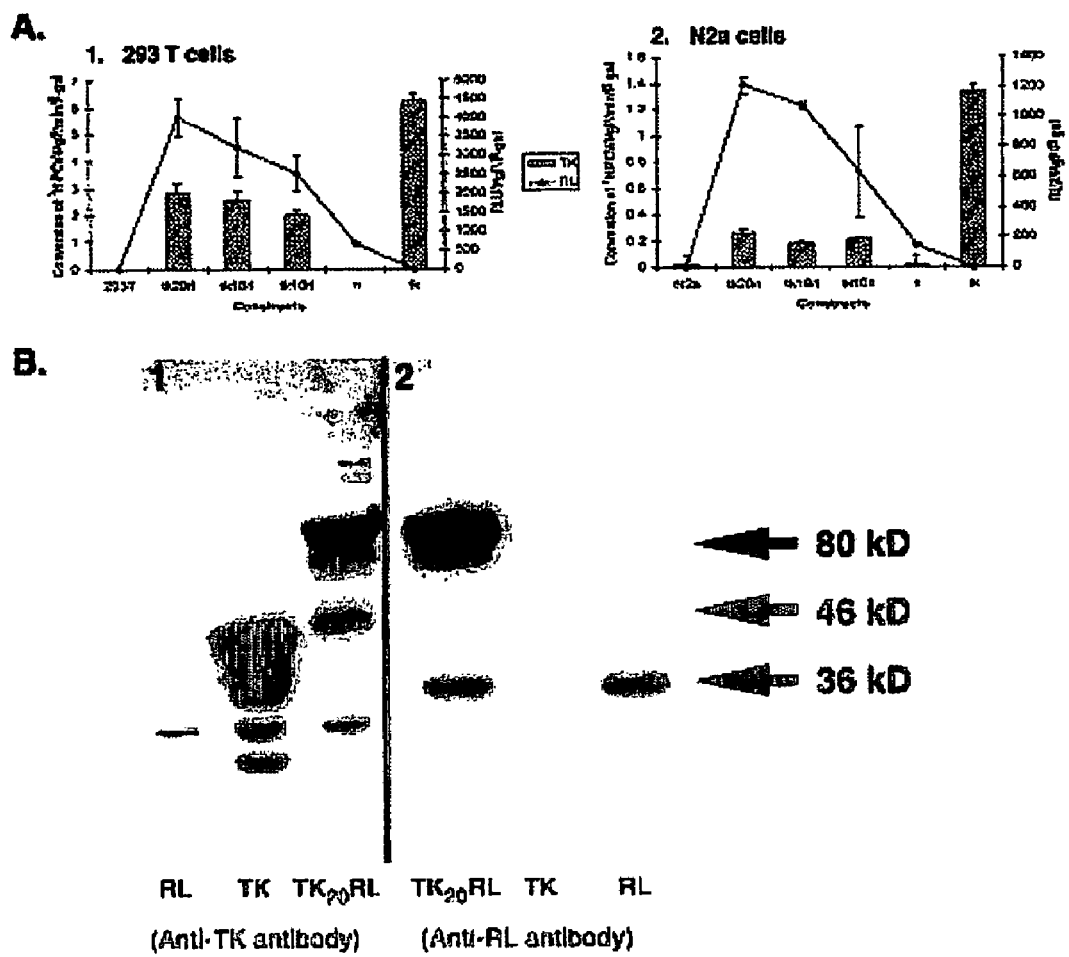
FIG. 2. Functional and biochemical characterization of TK-RL fusion proteins. A, TK and RL activity exhibited by the tk-rl fusion constructs in 293T (1) and N2a (2) cell lines. Cells were transiently transfected with tk20rl, tk18rl, tk10rl, CMVtk, CMV-rl, and CMV-β-gal and harvested at 24 h and assayed for the TK and RL enzyme activities. Values for TK and RL activity were normalized with β-GAL activity for each transfection. The TK activity is expressed as (percentage of conversion of 8-$^3$H-penciclovir to its phosphorylated form)/μg protein/min. The RL activity is expressed as relative light units/μg protein. Error bars represent SE for triplicate measurements. B, Western blot analysis of TK20RL fusion protein. Twenty μg of total cellular protein obtained from the cell lysates of transiently transfected 293T cells with tk20rl, tk, and rl plasmids were resolved in a 10% SDS polyacrylamide gel, transferred, and probed with (1) anti-TK and (2) anti-RL antibodies, respectively. Both the antibodies recognize the TK20RL fusion at ~80 kDa and also a 36-kDa (by anti-RL antibody) and a 46-kDa (by anti-TK antibody) fragment (first lanes of both 1 and 2) as a result of partial cleavage. The polyclonal anti-TK antibody and monoclonal anti-RL antibody also recognize TK at ~46 kDa (second lane from left in 1) and RL at ~36-kDa (third lane from the left in 2), respectively.

To compare the levels of reporter gene expression of each tk-rl fusion plasmids, three different cell lines [293T (FIG. 2A.1), N2a (FIG. 2A.2), and C6 (data not shown)] were transiently transfected with the three plasmids (tk20rl, tk18rl, or tk10rl) along with positive controls (pCDNA 3.1-tk and pCDNA3.1-rl) and negative controls (control cells mock transfected). Each cell line was also cotransfected with the β-gal reporter gene to normalize for transfection efficiency. After 24 h, the expression levels of all of the three reporter genes were assayed from the same cell lysates and TK and RL activities were normalized to β-GAL activity. Despite decreased TK enzyme activity seen by all of the fusion constructs in comparison to the positive control (pCDNA3.1-HSV1-sr39tk), a trend of increase in the level of TK activity with increasing spacer length is observed. The tk20rl plasmid (longest spacer) shows the highest TK activity, which is still 45% (293T; FIG. 2A.1), 19% (N2a; FIG. 2A.2), or 22% (C6; data not shown) of that of the positive control. Interestingly, the RL activity of each construct is relatively higher (~6-8 fold; FIGS. 2, A.1 and A.2) than the positive control (pCDNA3.1-rl) and also increases with increasing spacer length.

Western Blot Analysis of Extracts from Cells Transiently Transfected with tk20rl Probed with anti-TK and anti-RL Antibodies Reveals the Presence of an 80-kDa Fragment, the Predicted Size of the TK20RL Fusion.

To investigate tk20rl fusion reporter gene expression at the protein level, cell lysates from tk20rl-, tk-, and rl-transfected 293T cells were resolved by 10% SDS-PAGE and analyzed on Western blots by using antibodies specific for TK or RL (FIG. 2B). The predominant band recognized by both anti-TK and anti-RL antibodies is of 80 kDa, the expected size of the TK20RL fusion protein. However, in both cases, a weak band of similar size of either TK (or RL alone when probed with respective antibodies is seen. This is likely attributable to partial cleavage of the fusion protein. TK and RL proteins were recognized at ~46 and 36 kDa band by their specific antibodies. A semiquantitative analysis of the Western blot revealed that ~36 and 25% of the total fusion protein was cleaved into its TK and RL components, respectively. The lower molecular weight bands present in the positive TK sample might have resulted from partial degradation of the sample or nonspecific binding of the polyclonal anti-TK antibody to other cellular proteins.

Figure 3:
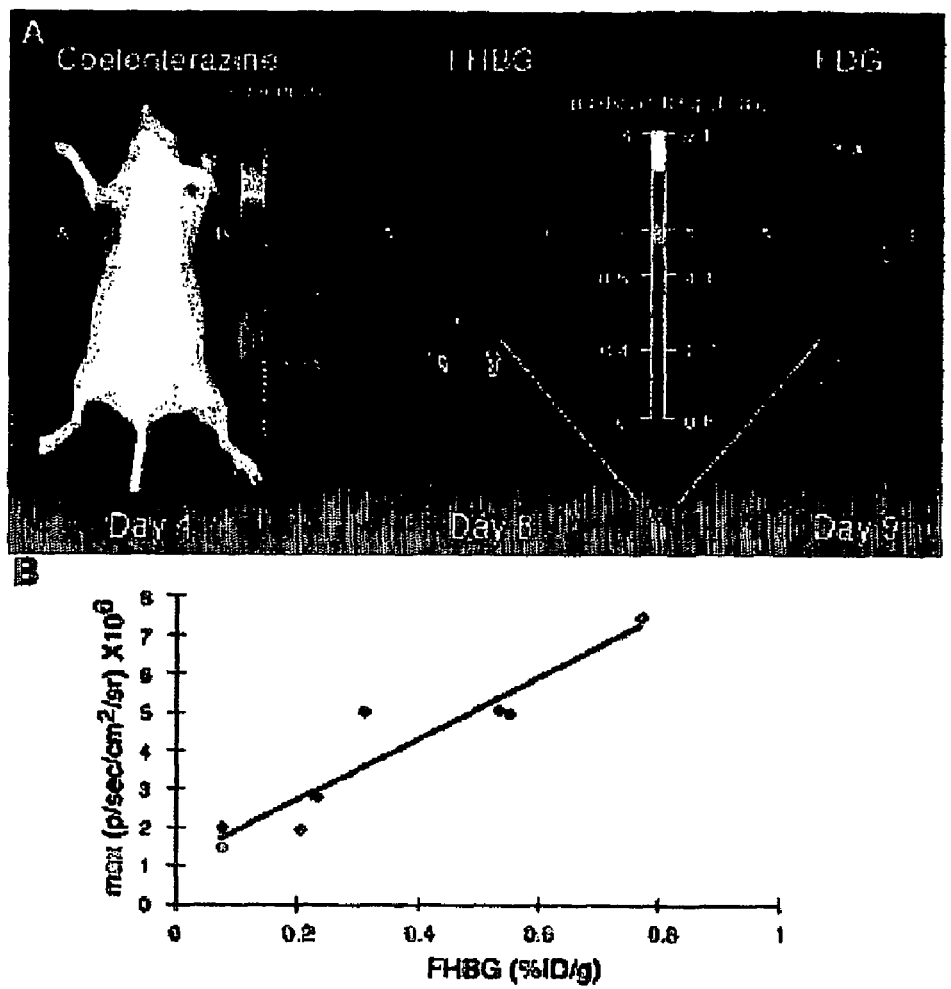
FIG. 3. In vivo imaging of tk20rl fusion protein by using two different modalities. A, optical and microPET imaging of tk20rl fusion construct in the same nude mouse. A total of 2×10$^6$ of N2a cells stably expressing the tk20rl fusion construct and control N2a cells was implanted s.c. on left and right shoulders in a nude mouse. After 4 days when each tumor was ~3-4 mm in diameter, the mouse was first scanned in the CCD camera after injection of coelenterazine via tail vein and bioluminescence signal was recorded as maximum p/sec/cm$^2$/sr (left panel). The same mouse was imaged 4 days later by microPET using FHBG (center panel) and again using FDG on the following day (right panel). The tumor formed by tk20rl-expressing cells shows high bioluminescence as well as FHBG accumulation in comparison to the control tumor. The FDG image represents the viability of both tk20rl and control tumor. Nonspecific accumulation of tracer was found in the gastrointestinal tracts (GI), bladder in case of FHBG (attributable to clearance of tracer), and in GI tract and brain in case of FDG (attributable to high metabolic activity). B, in vivo correlation of TK and RL gene expression exhibited by four clones of N2a cells stably but differentially expressing the tk20rl fusion. A total of 2×10$^6$ cells of each of four clones were implanted on the left shoulders of two nude mice each, and after 8-10 days, mice were imaged by microPET and optical CCD camera on the same day. Plot of % ID/g of FHBG versus bioluminescence signal as expressed as maximum (p/sec/cm$^2$/sr) obtained from the ROI drawn on the tumors of images ($r^2$=0.89). Each of the eight data point represents ROI data from the bioluminescent and PET image of the same mouse.

N2a Cells Stably Expressing the tk20rl Fusion Reporter Gene Can Be Imaged in Living Mice Using a Tumor Xenograft Model by both microPET and Optical-cooled CCD Imaging Systems. In order to test the efficacy of a fusion reporter vector for imaging of reporter gene expression quantitatively and repeatedly in living subjects using two different modalities, we isolated several clones of N2a cells stably expressing tk20rl fusion gene and one exhibiting the highest TK, and RL activity, and tested for its ability to be imaged in vivo using microPET and a cooled CCD camera in a tumor xenograft model. Five nude mice received s.c. injections in each shoulder with control N2a cells or tk20rl expressing cells. When the tumors attained a minimum of 0.6-0.7 cm in diameter, mice were first scanned using the cooled CCD camera followed by a microPET scan. Optical imaging of these mice after tail-vein injection of coelenterazine reveal that the tumors expressing the tk20rl fusion show relatively high bioluminescence of ~3081×10$^3$+725×10$^3$ maximum (p/sec/cm$^2$/sr) in comparison to the control N2a tumors [~3.1×10$^3$+0.7×10$^3$ maximum (p/sec/cm$^2$/sr), P<0.002; FIG. 3A]. Next, we scanned these mice by microPET using FHBG and finally on the following day using FDG. We quantified the signal from each tumor directly from the microPET images to determine the % ID/g for FDG and FHBG. This % ID/g is a measure of the amount of tracer accumulated in a given tissue site normalized to the injected amount and to the mass of the tissue examined. The FHBG accumulation in the tumors reflects the TK activity of the tk20rl-expressing cells, whereas the PDG accumulation reflects the metabolic activity of the tumor cells. The mean % ID/g value for FHBG accumulation in the tk20rl-expressing tumors (0.812+0.16) was significantly higher than the control N2a tumors (0.075+0.011; P<0.002) for the five mice. The mean FDG % ID/g values of tk20rl-expressing and -control tumors were not significantly different as expected (2.45±0.25 versus 2.6±0.18; FIG. 3A). Although the cell culture data showed a decrease in TK activity with the tk20rl fusion in comparison to HSV1-sr39tk, microPET imaging reveals easily detectable FHBG accumulation in the tumors expressing the TK20RL fusion protein.

We next examined whether tk and rl expression was correlated from the tk20rl fusion construct in living mice. Four clones of N2a cells stably but differentially expressing the fusion vector were implanted as tumors in eight nude mice (two mice for each clone) and microPET and optical CCD imaging of those mice were performed on the same day. The % ID/g values for FHBG and the bioluminescence signal of the tk20rl expressing tumors were well correlated ($R^2$=0.89) across the eight mice (FIG. 4B). The TK and RL activities of these four stable clones in vitro were also well correlated ($R^2$=0.91; data not shown).

Figure 4:
FIG. 4. Imaging serial increase in rl gene expression over time in tumors stably expressing the tk20rl fusion. A total of 2×10$^6$ of N2a cells stably expressing tk20rl fusion gene and control N2a cells was implanted on the left and right shoulders, respectively, of a single nude mouse and imaged daily using the optical CCD camera after injection of coelenterazine. A gradual increase in bioluminescence was observed in the tumor expressing tk20rl fusion over time but not in the control tumor.

Renilla Luciferase Reporter Gene Expression Can Be Serially Measured in Cells Stably Expressing the tk20rl Fusion Construct in Living Mice with High Sensitivity. One of the greatest advantages of optical bioluminescence imaging is its comparatively high sensitivity (allowing detection of low cell numbers) for imaging gene expression, whereas microPET imaging requires a greater tumor volume (3-5 mm) or mass of cells to obtain a detectable signal. We therefore implanted tk20rl-expressing and -nonexpressing control N2a cells as tumors on both the shoulders of four nude mice and imaged them daily using a cooled CCD camera to monitor the expression level of the fusion reporter construct. Significant signal is not seen on the first day (both the control N2a and tk20rl-expressing tumors showed bioluminescence value maximum at ~4×$10^3$ p/sec/$cm^2$/sr), but after the second day, the optical signal in the tk20rl-expressing tumors started increasing progressively and reached a maximum of 6×$10^6$+1.5×$10^6$ (p/sec/$cm^2$/sr) on day 10, whereas the signal in control tumors remained unchanged (12.0×$10^3$+4.2×$10^3$ maximum p/sec/$cm^2$/sr) throughout the study (FIG. 4). With the gradual increase in rl expression, we observed gradual growth of the tumors that attained a diameter of ~0.6-0.8 cm at day 10. We also attempted microPET imaging of these mice when the tumors were not palpable but were unable to obtain any detectable level of signal (data not shown). Presence of the bioluminescence rl reporter gene in the tk20rl fusion construct, therefore, confers a highly sensitive tool for monitoring reporter gene expression.

Discussion

The construction of a novel fusion gene vector is described, the vector harboring HSV1-sr39 thymidine kinase, a PET reporter gene and renilla luciferase, a bioluminescence reporter gene and its application in living mice using two different imaging modalities is validated. HSV1-thymidine kinase (both wild-type and the sr39 mutant) are well-established PET reporter genes (Jacobs, A., Voges, J., Reszka, R., Lercher, M., Gossmann, A., Kracht, L., Kaestle, C., Wagner, R., Wienhard, K., and Heiss, W. D. Positron-emission tomography of vector-mediated gene expression in gene therapy for gliomas. Lancet, 358: 727-729, 2001; Gambhir, S. S., supra, Proc. Natl. Acad. Sci. USA, 97: 2785-2790; Yu, Y., supra, Nat. Med., 6: 933-937) for imaging gene expression. Fusion vectors harboring wild-type tk and green gfp (tk-gfp) constructed by several groups (Wahlfors, J., Loimas, S., Pasanen, T., and Hakkarainen, T. Green fluorescent protein (GFP) fusion constructs in gene therapy research. Histochem. Cell Biol., 115: 59-65, 2001; Jacobs, A., Dubrovin, M., Hewett, J., Sena-Esteves, M., Tan, C. W., Slack, M., Sadelain, M., Breakefield, X. O., and Tjuvajev, J. G. Functional coexpression of HSV-1 thymidine kinase and green fluorescent protein: implications for noninvasive imaging of transgene expression. Neoplasia, 1: 154-161, 1999) could retain sufficient levels of TK activity and be imaged by microPET. As shown herein, the sr39thymidine kinase-renilla luciferase fusion vectors constructed by us could also maintain the TK and RL activities in different cell lines at different levels. However, our attempt to build a fusion construct of tk and fl yielded a poorly active fusion protein (unpublished data). Another triple fusion construct bearing wild-type tk, fl, and neomycin genes (tk-fl-neo; Strathdee, C. A., McLeod, M. R., and Underhill, T. M. Dominant positive and negative selection using luciferase, green fluorescent protein and beta-galactosidase reporter gene fusions. Biotechniques, 28: 210-212, 214, 2000) also showed very low TK activity in comparison to the tk vector alone in cell culture in our hands (unpublished data). Therefore, the nature of the fusion partner also affects the activity of the TK enzyme. Moreover the length of the spacer between the two proteins seems to play an important role in maintaining functionality of each protein, which has also previously been reported for various fusion constructs (Wahlfors, J., supra, Histochem. Cell Biol., 115: 59-65). In addition, it is likely that the amino acid (a.a.) sequence and composition of the spacer can influence the activities of either enzyme. The order of the fusion partners of the construct might also influence the activities of the proteins depending on the positioning of critical amino acids in the protein backbones. It has recently been shown that small changes in HSV1-tk, including several critical amino acids at the COOH-terminal end (Saijo, M., Suzutani, T., Niikura, M., Morikawa, S., and Kurane, I. Importance of C-terminus of herpes simplex virus type 1 thymidine kinase for maintaining thymidine kinase and acyclovir-phosphorylation activities. J. Med. Virol., 66: 388-393, 2002), make this enzyme more prone to loss in activity, suggesting care is needed in fusing proteins to the COOH terminus. The tk20rl fusion described in the current work has a decreased TK activity that might be improved by using a longer/different spacer between the two genes or placing tk as the downstream gene. On the other hand, this tk20rl fusion exhibits ~6-8-fold increase in RL activity in comparison to the rl alone that has made this fusion vector superior for bioluminescence imaging. However, a true comparison of the activities of the fusion protein with the nonfused control proteins can be made only after measuring the $K_m$ and $V_{max}$ for each protein. Future studies will need to purify each protein and study the substrate kinetics in a detailed fashion to better understand the effects of fusing the individual proteins on the proteins ability to act on substrate. Our results demonstrate that despite decreased TK activity, it is possible to image the TK20RL fusion protein noninvasively and repetitively in living mice both by microPET and by an optical CCD camera. Therefore, this fusion reporter gene has the potential to translate approaches from small animal models to preclinical and clinical applications. We know of only one report in the literature on measuring bioluminescence at the single cell level using fl (Hooper, C. E., Ansorge, R. E., Browne, H. M., and Tomkins, P. CCD imaging of luciferase gene expression in single mammalian cells. J. Biolumin. Chemilumin., 5: 123-130, 1990) that required a highly sensitive CCD camera attached to a microscope. We are currently exploring the possibility to image the tk20rl fusion reporter at the single cell level using a similar setup. However, this approach might not be as useful as fluorescence approaches for cell imaging because of the relatively high light yield of fluorescence approaches as compared with bioluminescence approaches, and thus we are currently validating a triple fusion construct harboring a fluorescence (gfp or red fluorescence protein), a bioluminescence (fl or rl), and a PET (sr39tk or wild-type tk) reporter gene (Ray, P., Min, J. J., and Gambhir, S. S. Multimodality imaging of reporter gene expression in single cells and living mice using a novel triple fusion vector. J. Nucl. Med., in press, 2003). Although approaches have been validated to image fluorescence reporter gene expression in small living animals (Yang, M., Baranov, E., Jiang, P., Sun, F. X., Li, X. M., Li, L. N., Hasegawa, S., Bouvet, M., Al-Tuwaijri, M., Chishima, T., Shimada, H., Moossa, A. R., Penman, S., and Hoffman, R. M. Whole-body optical imaging of green fluorescent protein expressing tumors and metastases. Proc. Natl. Acad. Sci. USA, 97: 1206-1211, 2000), bioluminescence reporter genes should exhibit several advantages for in vivo imaging in living animals. In contrast to fluorescence imaging, bioluminescence imaging is not limited by the autofluorescence properties of living cells, does not require any external source of light for activation, and rather depends on the delivery of specific substrates. Although there are reports of imaging fluorescence proteins in deep tissues of mice, these approaches often require special surgical procedures for exposing the animals. In contrast, we can easily detect and quantitatively and reproducibly evaluate the bioluminescence signal from various sites within the intact living mouse as described in our previous reports (Wu, J. C., Inubushi, M., Sundaresan, G., Schelbert, H. R., and Gambhir, S. S. Optical imaging of cardiac reporter gene expression in living rats. Circulation, 105: 1631-1634, 2002; Bhaumik, S., and Gambhir, S., supra, Proc. Natl. Acad. Sci. USA, 99: 377-382).

The fusion reporter gene described here may have some limitations because of partial cleavage (~25-35%) of the fusion into its two component proteins, which might result in a loss of sensitivity in different cell lines depending on the presence of specific proteases. However, the high correlation of TK and RL activities of the stably expressing cell lines in both in vitro and in vivo suggest that this fusion will be useful in monitoring tumor growth and cell trafficking studies where steady-state expression is expected. Future studies will need to explore alternate spacers to minimize cleavage of the fusion protein.

The higher sensitivity of optical imaging allows lower levels of reporter gene expression and/or lower numbers of expressing cells to be imaged relative to the PET approach. The sensitivity differences cannot be accounted for because of the reduced TK activity alone because this would only account for a 3-5-fold difference, and the number of cells detectable by optical imaging are several log-fold lower. We could follow reporter gene expression level using the fusion protein from a very early stage of s.c. implanted cells using the cooled CCD camera. Additional studies will be needed to better characterize the differences in sensitivity at various depths within a mouse. However, the drawback of bioluminescence imaging is this approach is not tomographic and difficult to translate into humans. Presence of the PET reporter gene in this fusion protein, on the other hand, is compatible with tomographic tools for measuring reporter gene expression that could also be used in larger subjects including humans. This fusion protein, therefore, provides a unique tool of validating different approaches quickly in small animal models at a very low number of cells that can be rapidly translated to clinical use. Future use of this fusion, including single cell imaging, should foster additional implementation of reporter genes directly from the cell to animal to human level. This, in turn, should lead to acceleration of many areas of cancer research, including cell trafficking, tumor therapy, and gene therapy.

EXAMPLE 2

Triple Fusion Reporter

Introduction: We have described the construction and validation of a double fusion reporter vector (tk20rl) (Example 1) carrying a mutant Herpes Simplex Virus thymidine kinase (sr39tk) PET reporter gene and a renilla luciferase (rl) bioluminescence optical reporter gene in living mice. In this Example, we describe the construction and testing of several triple fusion reporter genes compatible with bioluminescence, fluorescence and positron emission tomography (PET) imaging.

A triple fusion reporter vector harboring a bioluminescence synthetic Renilla luciferase (hrl) reporter gene, a reporter gene encoding the monomeric red fluorescence protein (mrfp1), and a mutant herpes simplex virus type 1 sr39 thymidine kinase [HSV1-truncated sr39tk (ttk); a PET reporter gene] was found to preserve the most activity for each protein component and was therefore investigated in detail. After validating the activities of all three proteins encoded by the fusion gene in cell culture, we imaged living mice bearing 293T cells transiently expressing the hrl-mrfp-ttk vector by microPET and using a highly sensitive cooled charge-coupled device camera compatible with both bioluminescence and fluorescence imaging. A lentiviral vector carrying the triple fusion reporter gene was constructed and used to isolate stable expressers by fluorescence-activated cell sorting. These stable 293T cells were further used to show good correlation ($R^2$~0.74-0.85) of signal from each component by imaging tumor xenografts in living mice with all three modalities. Furthermore, metastases of a human melanoma cell line (A375M) stably expressing the triple fusion were imaged by microPET and optical technologies over a 40-50-day time period in living mice. Imaging of reporter gene expression from single cells to living animals with the help of a single tri-fusion reporter gene will have the potential to accelerate translational cancer research.

Methods

Chemicals. [8-$^3$H]Penciclovir and $^{14}$C-labeled 2'-fluoro-5-fluoro-1-β-D-arbinofuranosyluracil were obtained from Moravek Biochemicals (Brea, Calif.). 9-(4-[18F]Fluoro-3-hydroxymethylbutyl)guanine (BG) was also synthesized at University of California Los Angeles as detailed previously (Yaghoubi, S., Barrio, J. R., Dahlbom, M., Iyer, M., Namavari, M., Satyamurthy, N., Goldman, R., Herschman, H. R., Phelps, M. E., and Gambhir, S. S. Human pharmacokinetic and dosimetry studies of [18F]FBG: a reporter probe for imaging herpes simplex virus type-1 thymidine kinase reporter gene expression. J. Nucl. Med., 42: 1225-1234, 2001). Coelenterazine was purchased from Biotium, Inc. (Hayward, Calif.). The polyclonal anti-TK antibody was a kind gift of Dr. M. Black (Washington State University, Pullman, Wash.), and the monoclonal anti-Renilla luciferase protein (RL) was purchased from Chemicon International (Temecula, Calif.).

Construction of hrl-mrfp-ttk and Other Fusion Genes. PCR amplification and standard cloning techniques were used to insert the hrl and mrfp genes from plasmid pCDNA 3.1-CMV-hrl (Promega, Madison, Wis.) and pCDNA3.1-CMV-mrfp1 in frame with the ttk gene into the pCDNA3.1-sr39-truncated tk (a kind gift of Dr. D. Kaufinan; University of California, Los Angeles, Calif.). The CMV-wtk vector was obtained from Dr. M. Black and modified to truncated wtk (wttk) by deleting first 135 bp through PCR and cloned in pCDNA3.1 backbone to generate CMV-wttk plasmid. CMV-fl and CMV-egfp were purchased from Promega and BD Sciences-Clontech (Palo Alto, Calif.) respectively. For PCR amplifications, different 5' and 3' end primers were used to generate the fusion vectors. Standard cloning techniques were used to generate the lentiviral (CS-hrl-mrfp-ttk) vector as performed previously in our laboratory (De, A., Lewis, X. H., and Gambhir, S. S. Noninvasive imaging of lentiviral-mediated reporter gene expression in living mice. Mol. Ther., 7: 681-691, 2003).

Cell Lines and Transient Transfection Procedures. Neuro 2a (N2a) neuronal cell lines (a gift from Dr. Vincent Mauro; Scripps Research Institute, La Jolla, Calif.), 293T human embryonic kidney cells (American Type Culture Collection, Manassas, Va.), and A375M human melanoma cells (a gift from Dr. M. Kolodny; University of California, Los Angeles, Calif.) were used. The N2a and A375M cells were cultured in high-glucose DMEM supplemented with 10% fetal bovine serum and 1% penicillin (100 µg/ml) and streptomycin (292 µg/ml), and 293T cells were grown in MEM supplemented with 10% fetal bovine serum and 1% penicillin/streptomycin solution. All transient transfections were carried out using the Superfect transfection reagent (Qiagen, Valencia, Calif.) following the protocol recommended by the manufacturer.

tTK, hRL, and β-Galactosidase (β-Gal) Activity. TK enzyme activity assays were performed as described previously (Gambhir, S. S., Bauer, E., Black, M. E., Liang, Q., Kokoris, M. S., Barrio, J. R., Iyer, M., Namavari, M., Phelps, M. E., and Herschman, H. R. A mutant herpes simplex virus type 1 thymidine kinase reporter gene shows improved sensitivity for imaging reporter gene expression with positron emission tomography. Proc. Natl. Acad. Sci. USA, 97: 2785-2790, 2000), and β-Gal and Renilla or firefly luciferase assays were done using the β-Gal enzyme assay system and Dual-Luciferase Reporter Assay System from Promega, respectively. Each of the luciferase reactions was measured in a TD 20/20 luminometer (Turner Designs, Sunnyvale, Calif.) for a period of 10 s.

Western Blot Analysis. The levels of tTK and hRL were evaluated by Western blotting with a rabbit polyclonal anti-TK antiserum and a mouse monoclonal anti-Renilla antibody using cell lysates prepared from 293T cells transfected with CMV-hrl-mrfp-ttk, CMV-ttk, and CMV-hrl plasmids.

Lentiviral Production. Lentivirus was developed and used to infect 293T and A375M cells as described previously (De, A., Lewis, X. H., and Gambhir, S. S. Noninvasive imaging of lentiviral-mediated reporter gene expression in living mice. Mol. Ther., 7: 681-691, 2003).

Fluorescence Microscopy, CCD Imaging, and FACS. Expression of mRFP1 was observed under a Zeiss Axiovert 200M fluorescence microscope (Carl Zeiss Microimaging Inc., Thomwood, N.Y.) with DsRed filter setting ($\lambda_{ex}$, 546 nm; $\lambda_{em}$, 605 nm) and analyzed with MetaMorph software (University Imaging Corp., Downingtown, Pa.). For quantification of the expression level of mRFP1 present in the CMV-hrl-mrfp-ttk and CMV-mrfp1, $1\times10^4$ and $1\times10^5$ of 293T, A375M, or N2a cells expressing the vectors were seeded in black-bottomem clear 96-well plates and imaged in the Xenogen IVIS optical imaging system (Xenogen Corp., Almeda, Calif.) with an excitation filter at 500-550 nm and an emission filter at 575-650 nm. Regions of interest (ROIs) were drawn over the cell area and quantified by using Living Image Software version 2.20. For FACS, $1\times10^6$ of CS-hrl-mrfp-ttk infected 293T and A375M cells were sorted by using a Becton Dickinson FACSvantage SE cell sorter.

MicroPET Imaging of Mice. Animal care and euthanasia were performed with the approval of the University of California Animal Research Committee. Male 12-14-week-old nude mice (nu/nu) received s.c. injection with ~$10\times10^6$ 293T cells transiently expressing the CMV-hrl-mrfp-ttk fusion, CMV-ttk, CMV-hrl, and CMV-mrfp1 on the ventral side, and mice (n=4) were scanned the next day using a microPET as described previously (Gambhir, S. S., supra, Proc. Natl. Acad. Sci. USA, 97: 2785-2790). Additionally, $10\times10^6$ of each of four differentially expressing clones of 293T cells stably expressing hrl-mrfp-ttk gene were implanted in three mice and scanned in the microPET ~24 h later. The microPET images were reconstructed by using three-dimensional filtered back projection and an iterative maximum a posteriori algorithm (Qi, J. Y., Leahy, R. M., Cherry, S. R., Chatziioannou, A., and Farquhar, T. H. High-resolution 3D Bayesian image reconstruction using the microPET small-animal scanner. Phys. Med. Biol., 43: 1001-1013, 1998). ROIs were drawn over the tumor area. The ROI counts were converted to percentage of injected dose/g (ID/g) using filtered back projection as described previously (Gambhir, S. S., supra, Proc. Natl. Acad. Sci. USA, 97: 2785-2790), and images shown were reconstructed with maximum a posteriori algorithm.

Bioluminescence and Fluorescence Imaging of mRFP1 and RL Expression in Living Mice. For in vivo fluorescence imaging, mice implanted with the cells described above were anesthetized, and each mouse was placed in a light tight chamber equipped with a halogen light source, and whole body image was acquired for 1 s using the Xenogen IVIS optical imaging system with an excitation filter at 500-550 nm and an emission filter at 575-650 nm. ROIs were drawn over implanted cell area and quantified by using Living Image Software version 2.20. For bioluminescence imaging, each mouse next received injection with 10 µl (2 µg/µl dissolved in methanol) of coelenterazine diluted in 90 µl of PBS (pH 7) via tail vein. Each animal was then placed supine in the same light tight chamber, and whole body images were obtained and quantified as described previously (Bhaumik, S., and Gambhir, S. S. Optical imaging of Renilla luciferase reporter gene expression in living mice. Proc. Natl. Acad. Sci. USA, 99: 377-382, 2002). Both bioluminescence and fluorescence signals were recorded as maximum [photons/second/centimeter$^2$/steradian (photons/s/cm$^2$/sr)].

Multimodality Imaging of Cancer Metastasis in Living Mice Using a Human Melanoma Cell Line (A375M) Stably Expressing the Triple Fusion Vector. Three 8-week-old Beige severe combined immunodeficient mice received injection with $7\times10^5$ A375M cells stably expressing the hrl-mrfp-ttk gene via tail vein and were imaged repeatedly with fluorescence, bioluminescence, and microPET. At day 40, the mice were first imaged with microPET and bioluminescence (as described above) and then sacrificed and imaged; the chest was cut open with Illuminatool Tunable lighting system using the 540 nm excitation filter and RFP viewing glass (Lightools Research). Fluorescence imaging and light photograph of mice were digitally captured with a Nikon camera for 2 s.

Results

A Multimodality Fusion Vector Harboring the hrl Gene (Bioluminescence), Gene Encoding for mRFP1 (Fluorescence), and a Mutant Truncated HSV1-sr39 Thymidine Kinase (PET) Reporter Gene Maintains hRL, mRFP1, and tTK Activity in Several Cell Lines. We first constructed a fusion gene vector (hrl-ttk) carrying hrl (hrl, gene; hRL, enzyme) and ttk (ttk, gene; tTK, enzyme) reporter genes separated by a 22-aa-long spacer (LENSHASAGYQACG-TAGPGSTG) (SEQ ID NO: 8) and then inserted the PCR-amplified mrfp1 gene fragment in the middle of the spacer (at the position of Cys-Gly) to generate a hrl-mrfp-ttk triple fusion reporter gene. The PCR-amplified hrl gene fragments from pCMV-hrl vector were inserted in frame with ttk gene (the first 45 aa of sr39tk gene were truncated to delete the nuclear localization signal of tk gene) cloned in pCDNA3.1+ separated by the above-mentioned spacer under the control of a CMV promoter. The resultant vector was then digested with HindIII and SacII and ligated in frame to PCR-amplified and HindIII/SacII-digested mrfp1 fragments (without stop codon) from pRSETB vector to generate the hrl-mrfp-ttk fusion vector. The order of the thee different reporter genes and spacers in this triple fusion vector is as follows: hrl-spacer (LEN-SHASAGYQAST) (SEQ ID NO: 9) -mrfp-spacer (TAGPG-SAT) (SEQ ID NO: 10) -ttk gene. The final vector was fully verified by sequencing.

Plasmid DNA prepared from four to five clones of CMV-hrl-mrfpttk triple fusion were transiently transfected in 293T cells, and the cells were first observed in a fluorescence microscope for mRFP1 activity and further assayed for hRL and tTK activity. The plasmid clone exhibiting the highest mRFPI, hRL, and tTK activities was selected for additional studies. To extend our study to different variants of bioluminescence/fluorescence/PET reporter genes, we also generated several functionally active multimodality reporter fusion vectors, i.e., fl-mrfp-ttk [by replacing hrl with firefly luciferase (fl)], fl/hrl-egfp/rfp-ttk (mrfp1 is replaced with egfp or tetrameric rfp known as DsRed2), and fl/hrl-rfp-wttk [by replacing the truncated HSV1-sr39tk (ttk) with wild-type HSV1-truncated thymidine kinase (wttk)]. The nature and the order of the spacers for all these constructs were equivalent to CMV-hrl-mrfp-ttk vector described earlier. The ttk, wttk, fl, hrl, rfp, gfp, and mrfp1 genes were also cloned in pCDNA3.1+backbone to generate positive control plasmids to directly compare the results of each fusion. All these fusion vectors were functionally active with respect to each individual protein, however the level of activity varied for each construct (Table 1). Overall, the hrl-mrfp-ttk fusion construct showed the highest activity for all three of the component proteins in comparison with other vectors and thus was further studied for multimodality imaging.

TABLE 1

Fluorescent, bioluminescent and PET* reporter gene expressions exhibited by different triple fusion constructs in comparison to the respective positive controls assayed from transiently transfected 293T cells (tTK and hRL activities are normalized with cotransfected β-Gal activity)

| Constructs | % TK activity | % uTK activity | % hRL activity | % FL activity | RFP/eGFP/mRFP (fluorescence activity by microscopy) |
|---|---|---|---|---|---|
| hrl-rfp-ttk | 39.7 | | 27.8 | | Medium |
| fl-rfp-ttk | 20.6 | | | 22.1 | Low |
| hrl-egfp-ttk | 50 | | 33 | | High |
| fl-egfp-ttk | 43 | | | 20 | High |
| hrl-mrfp-ttk | 149 | | 54 | | High |
| fl-mrfp-ttk | 100 | | | 53.6 | Medium |
| hrl-rfp-wttk | | 76 | 44.7 | | Medium |
| fl-rfp-wttk | | 61.6 | | 62.6 | Low |
| ttk | 100 | | | | |
| wttk | | 100 | | | |
| hrl | | | 100 | | |
| fl | | | | 100 | |
| mrfp1 | | | | | Very high |

*PET, position emission tomography; eGFP, enhanced green fluorescence protein; β-Gal, β-galactosidase.

Figure 5:
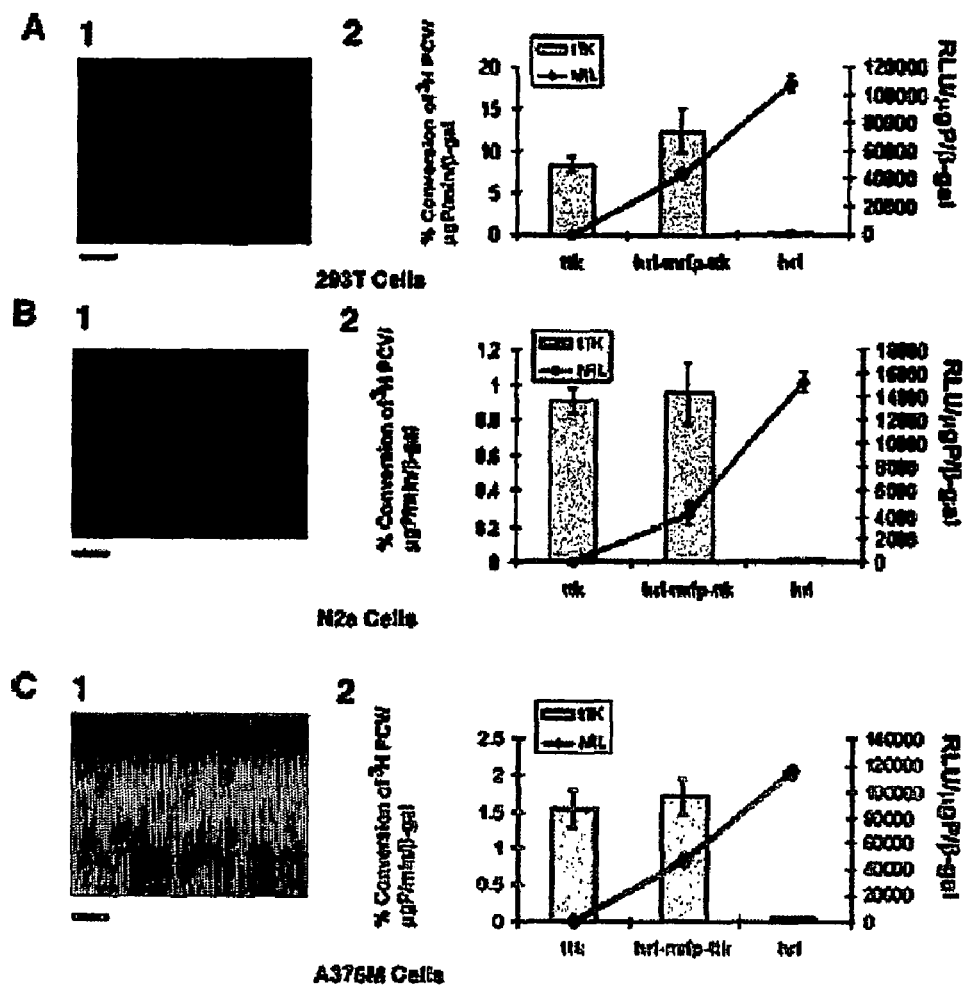
FIG. 5. mRFP1, hRL, and tTK activity exhibited by 293T, N2a, and A375M cell lines transiently transfected with the hrl-mrfp-ttk fusion construct. 293T (A), N2a (B), and A375M (C) cells were transiently cotransfected with CMV-β-gal and either CMV-hrl-mrfp-ttk, CMV-ttk, CMV-hrl, or CMVmrfp1; harvested 24 h later; and assayed for mRFP1 expression (A.1, B.1, and C.1; by fluorescence microscopy) and tTK/hRL enzyme activities (A.2, B.2, and C.2). Bars for the fluorescence micrographs represent 100 μm. Values for tTK and hRL activity were normalized with β-galactosidase activity for each transfection. The tTK activity is expressed as (percentage of conversion of [8-$^3$H]penciclovir to its phosphorylated form)/μg protein/min. The hRL activity is expressed as relative light units (RLU)/μg protein. Error bars represent SE for triplicate measurements. The slightly higher tTK activity exhibited by the hRL-mRFP-tTK fusion protein in comparison with the positive tTK protein is not statistically significant; however, the hRL activity of the hRLmRFP-tTK fusion protein is significantly lower (P<0.05) than the positive hRL protein.

To compare the levels of reporter gene expression of each of the components of the CMV-hrl-mrfp-ttk plasmid, three different cell lines [293T, N2a, and A375M (FIG. 5, A-C) were transiently transfected with the triple fusion plasmid along with proper positive controls (pCDNA3.1-ttk, pCDNA3.1-mfrp1, pCDNA3.1-hrl) and negative controls (mock-transfected control cells). Each cell line was also cotransfected with the CMV-β-gal reporter gene to normalize for transfection efficiency. After 24 h, the expression of mrfp1 was observed in the inverted fluorescence microscope, and then activity of the other three reporter genes was assayed from the same cell lysates, and tTK and hRL activities were normalized to β-Gal activity. In all three of the different cell lines, CMVhrl-mrfp-ttk showed equal or slightly higher tTK activity (not statistically significant) compared with the positive control (pCDNA3.1-ttk) but had a lower hRL activity [33% (A375M), 27.4% (N2a), and 54% (293T)] compared with that of the positive control pCDNA3.1-hrl plasmid (P<0.05). The expression level of mrfp1 of this triple fusion vector in all of the cell lines was ~60-70% of the positive control pCDNA3.1-mrfp1 vector, as determined by the fluorescence signal using the CCD camera.

Figure 6:
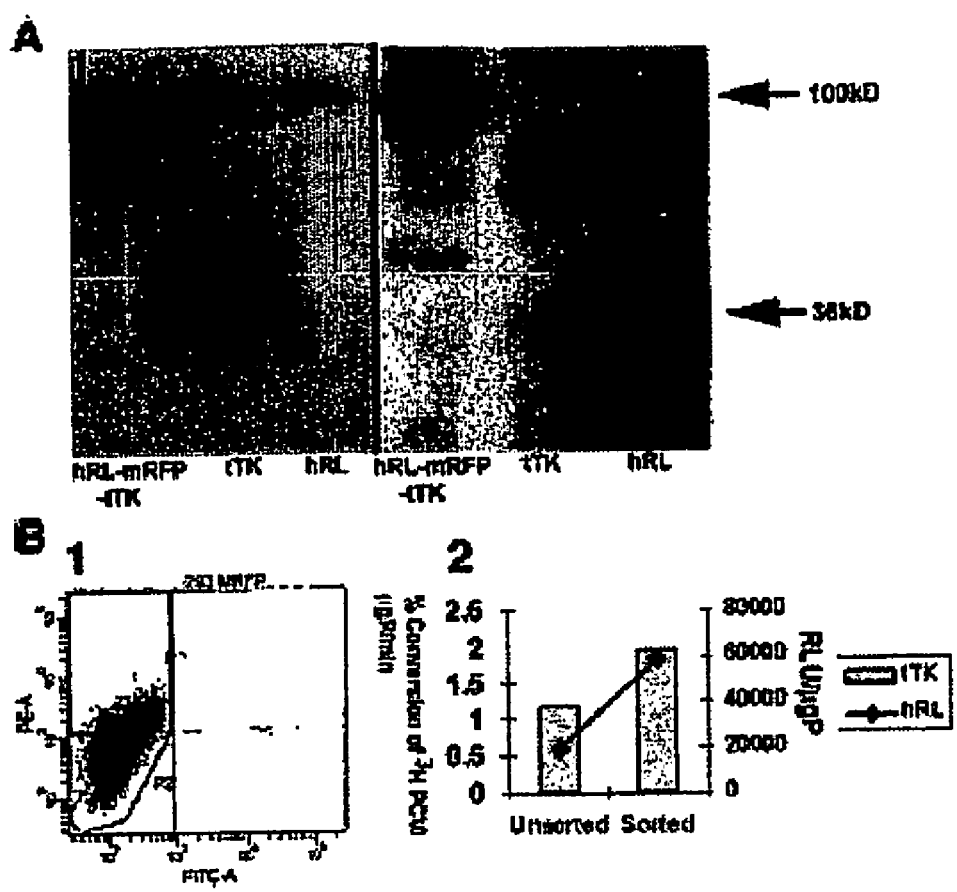
FIG. 6. Biochemical and flow cytometric characterization of hrl-mrfp-ttk fusion reporter gene expression. A, Western blot analysis of hRL-mRFP-tTK fusion protein. Twenty μg of total cellular protein obtained from the cell lysates of transiently transfected 293T cells with hrl-mrfp-ttk, ttk, and hrl plasmids were resolved in a 10% SDS polyacrylamide gel and transferred and probed with anti-TK (A.1) and anti-RL (A.2) antibodies. A 100-kDa band was specifically recognized by the antibodies only from the hRL-mRFP-tTK fusion samples. The polyclonal anti-TK and the monoclonal anti-RL antibody recognize tTK (second lane in A.1) and hRL (third lane in A.2) at about 36 kDa, respectively. B, flow cytometry plot and enzymatic activities of the positive expressers of CS-hrl-mrfp-ttk (lentiviral vector)-infected 293T cells. One million 293T cells were infected with CS-hrl-mrfp-ttk vector and sorted with fluorescence-activated cell sorting with a filter at 585±42 nm band setting. Highly fluorescing cells (~33%) that migrated to the P3 sector (B.1) were collected and further tested for tTK and hRL enzyme activities (B.2). The sorted fraction showed higher tTK and hRL activities than the unsorted population. The TK activity is expressed as (percentage of conversion of [8-$^3$H]penciclovir to its phosphorylated form)/μg protein/min. The RL activity is expressed as relative light units (RLU)/μg protein.

Western Blot Analysis of Extracts from Cells Transiently Transfected with hrl-mrfp-ttk Probed with Anti-TK and Anti-RL Antibodies Reveals the Presence of a 100-kDa Fragment, the Predicted Size of the Protein Encoded by the hrl-mrfp-ttk Fusion. To investigate hrl-mrfp-ttk fusion reporter gene expression at the protein level, cell lysates from hrl-mrfp-ttk-, ttk-, and hrl-transfected 293T cells were resolved by 10% SDS-PAGE and analyzed on Western blots by using antibodies specific for TK and RL (FIG. 6A). The predominant band in the triple fusion sample recognized by anti-TK (FIG. 6A.1) and anti-RL (FIG. 6.A.2) antibodies is about 100 kDa, the expected size of the hRL-mRFP-tTK fusion protein. The tTK and the hRL proteins were recognized at about 36 kDa band by their specific antibodies. Similar results were also obtained from N2a and A375M cell extracts (data not shown).

A Lentiviral Vector Carrying the hrl-mrfp-ftk Triple Fusion Is Able to Stably Transfect 293T and A375M Cells, and the Positive Expressers Can Be Sorted by FACS Analysis. One potential use of a lentiviral vector is to deliver the genes of interest to any type of dividing or nondividing cell lines or target tissues in living animals. Therefore, the full-length fusion gene cassette was cloned in the NheI and XhoI site of a second-generation lentiviral vector (De, A., Lewis, X. H., and Gambhir, S. S, supra, Mol. Ther., 7: 681-691), and viruses carrying the triple fusion reporter gene were used to transduce 293T cells. Five million 293T cells infected with lentivirus were sorted by FACS using a 585±42 nm filter setting, and 33% positive expressers were collected (FIG. 6B.1). The sorted and unsorted cells were then assayed for tTK and hRL expression (FIG. 6B.2) and clearly show a significant (P<0.05) gain in expression in the sorted cell population. Similarly, the A375M cells were transduced with the lentivirus carrying the triple fusion reporter gene, and positive expressers were selected by two rounds of FACS sorting and verifed to have significant hRL and tTK activities (data not shown).

293T Cells Transiently Expressing the hrl-mrfp-ttk Fusion Reporter Gene Can Be Imaged in Living Mice with the MicroPET and Optical Cooled CCD Imaging Systems. In order to test the fusion reporter vector for its efficacy in simultaneous imaging of reporter gene expression quantitatively and repeatedly in living subjects using different modalities, we injected $10 \times 10^6$ 293T cells transiently transfected with either CMV-hrl-mrfp-ttk, CMVttk, CMV-hrl, or CMV-mrfp1 vectors s.c. at four different sites on the ventral sides of four 12-14-week-old nu/nu nude mice. The mice were first scanned using the cooled CCD camera for fluorescence followed by a bioluminescence scan after injection of 20 μg of coelenterazine via tail vein. Fluorescence imaging of these mice reveals that the cells expressing the hrl-mrfp-ttk fusion (FIG. 7A.1, a) show lower fluorescence [~$11.03 \pm 6.03 \times 10^8$ maximum (pls/cm$^2$/sr)] in comparison with the cells expressing mrfp1 vector (FIG. 7A.1, c) alone [~$65.8 \pm 32.29 \times 10^8$ maximum (p/s/cm$^2$/sr); FIG. 7A.1]. No significant signal is observed from the other two sites of implantation carrying the CMV-ttk (FIG. 7A.1, b)—and CMV-hrl (FIG. 7A.1, d)—expressing cells. A bioluminescence scan of the mice shows a signal of $5.8 \pm 3.7 \times 10^6$ maximum (pls/cm²/sr) from the cells expressing the fusion reporter gene (FIG. 7A.2, a) and about 7.37±4×10⁶ maximum (p/s/cm²/sr) from the CMV-hrl-expressing cells (FIG. 7A.2, d). Similar to fluorescence imaging, the other two sites carrying CMV-mrfp1 (FIG. 7A.2, c)—and CMV-ttk (FIG. 7A.2, b)—expressing cells did not show any significant bioluminescence signal. Because the FHBG mass used for PET imaging is 1000-fold lower (due to the presence of radioactive isotope) than the coelenterazine mass used for bioluminescence imaging, PET imaging is not as sensitive as bioluminescence at superficial depths. Furthermore, PET imaging benefits from well-vascularized tissues with relatively high levels of reporter gene expression. We therefore implanted the cells expressing the fusion gene and ttk gene in the right and left axillary region of the mice. We quantified the signal from each of the sites expressing the CMV-hrl-mrfp-ttk and CMV-ttk directly from the microPET images to determine the percentage of ID/g tumor for FHBG. This percentage of ID/g is a measure of the amount of tracer accumulated in a given tissue site normalized to the injected amount and to the mass of the tissue examined. The mean percentage of ID/g for FBG accumulation in the CMV-hrlmrfp-ttk-expressing cells (0.303±0.09; FIG. 7A.3, a and FIG. 7A.4, a) did not differ significantly from that of the CMV-ttk-expressing cells (0.313±0.09; FIG. 7A.3, b and FIG. 7A.4, b) for the four mice (FIGS. 7A.3 and 7A.4). Preservation of a high level of tTK activity and moderate levels of hRL and mRFP1 activities by this tri-fusion vector thus allows simultaneous imaging of transient expression of all three of the reporter genes in living mice with all three of the imaging techniques. Repetitive imaging of the same mouse over a 10-day period produced signals for all three of the reporter genes that increased with time as the tumor burden increased (data not shown).

Figure 7:
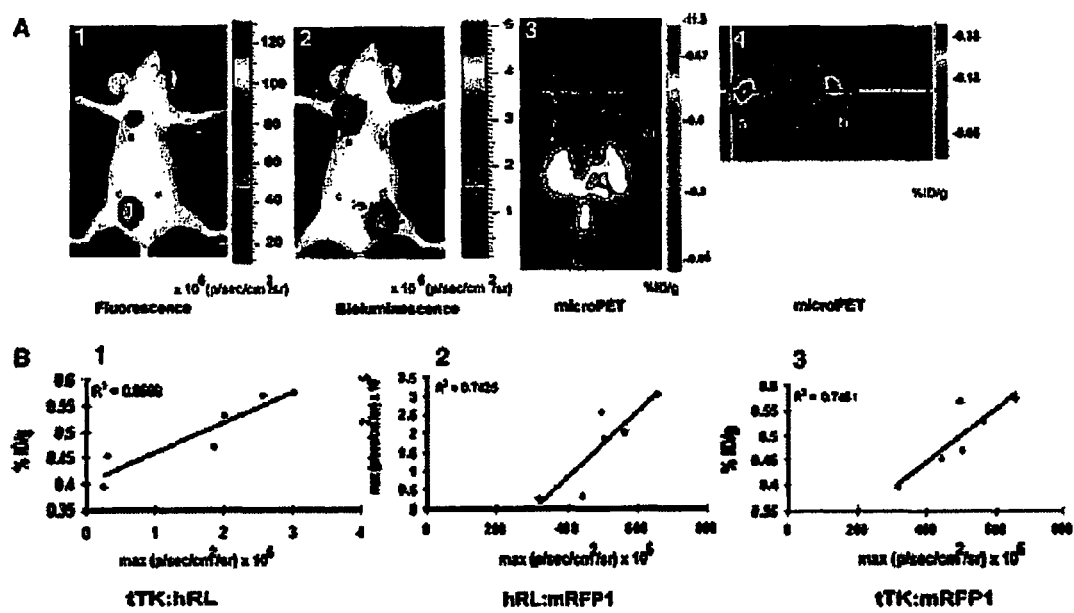
FIG. 7. Results of imaging living mice. A, fluorescence, bioluminescence, and micro-positron emission tomography (PET) imaging of hrl-mrfp-ttk expression in the same living nude mouse. Ten million 293T cells transiently expressing the CMV-hrl-mrfp-ttk, CMV-ttk, CMV-mrfp1, and CMV-hrl plasmids were implanted s.c. at four sites on the ventral side of a nude mouse and imaged the next day for fluorescence/bioluminescence and PET using a cooled charge-coupled device (CCD) camera and microPET, respectively. Fluorescence imaging was performed by placing the mouse in a CCD camera for 1 s, and a fluorescence image was acquired with a excitation filter at 500-550 nm and an emission filter at 575-650 nm. Cells expressing the fusion (A.1, a) and mrfp1 (A.1, c) genes showed fluorescence, and the signal is recorded as maximum photons/sec/cm$^2$/sr (A.1). The same mouse was then scanned in the CCD camera for bioluminescence after injection of coelenterazine via tail vein, and bioluminescence signal was found in cells expressing the fusion (A.2, a) and hrl (A.2, d) and recorded as maximum photons/sec/cm$^2$/sr (A.2). After the optical scan, the same mouse was imaged by micro-PET using 9-(4-[$^{18}$F]fluoro-3-hydroxymethylbutyl)guanine (FHBG). Cells expressing the fusion reporter gene (A.3, a and A.4, a) and ttk gene (A.3, b and A.4, b) showed FHBG accumulation in coronal section (A.3) and trans-axial section (A.4). Nonspecific accumulation of tracer was found in the gastrointestinal tracts and bladder (attributable to clearance of FHBG; A.3). B, in vivo correlation of hrl, mrfp1, and ttk gene expression exhibited by four clones of 293T cells stably but differentially expressing the hrl-mrfp-ttk fusion. Ten million cells of each clone were implanted on the axillary regions of the ventral side of three nude mice (two clones in each mouse), and after 24 h, mice were imaged by the cooled CCD camera and microPET. Plots of percentage of ID/g versus bioluminescence [expressed as maximum photons/second/centimeter$^2$/steradian (p/s/cm$^2$/sr); B.1], bioluminescence versus fluorescence (both expressed as maximum p/s/cm$^2$/sr; B.2), and percentage of ID/g versus fluorescence (expressed as maximum p/s/cm$^2$/sr; B.3) were obtained from the regions of interest drawn over the regions of cell implantation. Each of the six data points of each plot represents region of interest data from the fluorescence, bioluminescence, and microPET images of the same living mouse, with a total of three mice (2 points/mouse).

The lentivirus-infected 293T cells stably expressing the hrl-mt-ttk fusion gene described in the previous section were diluted to single cells, and four clones with differential expression of all three genes were selected. In cell culture, these four clones exhibited good correlation between tTK and hRL ($R^2=0.96$), hRL and mRFP1 ($R^2=0.94$), and tTK and mRFP1 ($R^2=0.86$) activities (data not shown). For quantification of mRFP1 activity, 3.5×10⁵ cells of each clone and 293T cells were seeded in black, clear-bottomed 96-well plates in triplicate and imaged in the CCD camera with DsRed2 excitation and emission filter options. ROIs were drawn on each well, and fluorescence was measured quantitatively for each group. The basal fluorescence exhibited by 293T cells was subtracted from the fluorescence of each well of each clone, and the mean of the three wells of each clone was taken as absolute fluorescence activity, expressed as maximum (p/s/cm²/sr) for each clone. tTK and hRL assays were performed as described earlier. To measure the correlation between the expression of the three reporter genes across three different imaging modalities, 10×10⁶ cells of each clone were implanted on the two axillary regions on the ventral side of three nude mice (two clones in each mouse), and mice were imaged for fluorescence, bioluminescence, and microPET on the same day as described above. The fluorescence and bioluminescence signals and the percentage of ID/g values for FHBG of the hrl-mrfp-ttk expressing clones across the three mice were all well correlated: $R^2=0.85$ (hRL:tTK; FIG. 7B.1); $R^2=0.74$ (hRL:mRFP1; FIG. 7.B.2); and $R^2=0.74$ (tTK:mRFP1; FIG. 7B.3).

Figure 8:
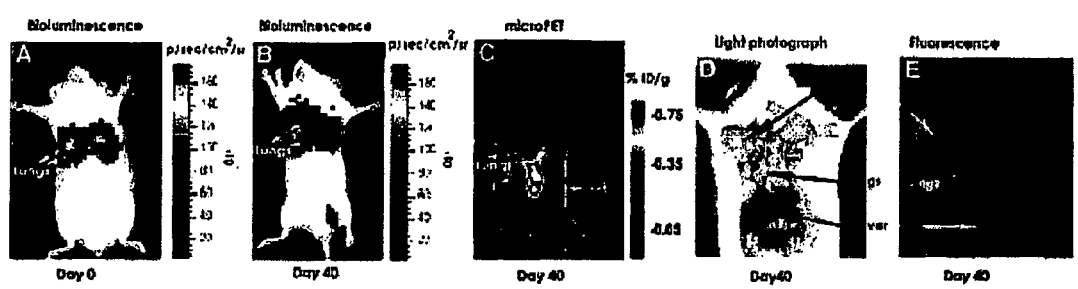
FIG. 8. Multimodality imaging of metastasis of A375M cells stably expressing the hrl-mrfp-tk fusion reporter gene in living mice. A, bioluminescence imaging of a SCID mouse injected with A375M cells expressing the hrl-mrfp-ttk vector at day 0. $7\times10^5$ A375M cells stably expressing the triple fusion were injected via tail-vein in a SCID mouse and two hours later imaged for bioluminescence signal following tail-vein injection of coelenterazine. Prominent bioluminescence signal was found from the region of both the lungs [1.3-1.5×10$^5$ max (p/sec/cm$^2$/sr)]. B, bioluminescence imaging of the same SCID mouse at day 40. At day 40, the same mouse was imaged and relatively high bioluminescence signal [2×10$^5$ max (p/sec/cm$^2$/sr)] was found from the left lung region and moderate signal from the right lung region. A faint bioluminescence signal (5×10$^3$ p/sec/cm$^2$/sr) was also present from the right pelvic region. C, microPET imaging of the same SCID mouse at day 40. Following a bioluminescence scan, the mouse was imaged in microPET using FHBG. Shown is a thin coronal slice of ~1-mm thickness. A strong signal (~0.78% ID/g) was present from the chest region (Ch) with lower signal (0.35% ID/g) from the lung region. The stronger PET signal was found to be from a metastatic tumor present deep inside the body, as evident from the fluorescence photograph (8.E). Note the gallbladder (GB) retains FHBG so background signal from the GB is also seen in the microPET images. D, light photograph of the same SCID mouse after sacrifice and organ exposure (image has been modified by using Adobe Photoshop version 6). E, whole body fluorescence imaging of the same SCID mouse. Fluorescing metastatic tumors were found in lung and chest regions that correspond with the bioluminescence and PET images.

Metastasis of A375M Human Melanoma Cells Expressing the hrl-mrfp-ttk Reporter Gene Can Be Imaged by MicroPET and an Optical CCD Camera in Living Mice. To apply the tri-fusion strategy to a relevant preclinical cancer study, we used a melanoma metastatic model. A375M human melanoma cells are known to metastasize to other organs once injected in the animal i.v. and form pulmonary and brain metastases with some rare occurrence of bone metastases. A375M cells (7×10⁵) stably expressing the hrl-mrfp-ttk reporter gene were injected in three 8-week-old Beige severe combined immunodeficient mice via tail vein. On the first day of cell injection, bioluminescence signal was detectable from the lungs (the primary route of cell migration; FIG. 8A), but not from microPET images (data not shown). The mice were then subsequently imaged over time every 67 days for a period of 40-50 days. At day 40, moderate microPET signal (~0.35% ID/g) from the lungs and strong signal (~0.78% ID/g) from the chest region are detected from one of the three mice (FIG. 8C). A corresponding bioluminescence signal (2×10⁵ p/s/cm²/sr) is detected from the lungs of the same mouse on the same day (FIG. 8B). The relatively high PET signal from the chest region (FIG. 8C) is not evident with bioluminescence imaging (FIG. 8C), likely due to relatively poor penetration of light produced by Renilla luciferase from greater depths. A faint bioluminescence signal (5×10³ p/s/cm²/sr) was also seen from the pelvic region of the mouse that was undetectable in microPET, likely due to hindrance by the nonspecific signal due to FHBG tracer clearance from the kidneys and gastrointestinal tract. In vivo fluorescence imaging of metastases did not produce good images due to significant autofluorescence caused by the presence of hair. However, when the mouse was sacrificed, and internal organs were exposed, several small metastatic tumors were found with fluorescence (FIG. 8E). Among the other two mice, one showed bioluminescence signal in the abdominal region at day 48; however we could not detect specific microPET signal, likely due to the presence of moderate levels of nonspecific signal resulting from the clearance of FHBG through kidneys and the gastrointestinal tract.

Discussion

We describe herein the construction of several novel triple fusion reporter genes including one harboring a bioluminescence reporter gene (synthetic Renilla luciferase), a fluorescence reporter gene (monomeric red fluorescence protein), and a PET reporter gene (truncated version of HSV1-sr39 thymidine kinase) and validate its application in living cells (cell microscopy and FACS) and in living mice using three different small animal imaging technologies (in vivo fluorescence, in vivo bioluminescence, and microPET). Use of bifusion reporter genes for molecular imaging has been validated previously by us (see Example 1; see also, Ray, P., Wu, A., and Gambhir, S. Optical bioluminescence and positron emission tomography imaging of a novel fusion reporter gene in tumor xenografts of living mice. Cancer Res., 63: 1160-1165, 2003) and by other investigators (Jacobs, A., Dubrovin, M., Hewett, J., Sena-Esteves, M., Tan, C. W., Slack, M., Sadelain, M., Breakefield, X. O., and Tjuvajev, J. G. Functional coexpression of HSV-1 thymidine kinase and green fluorescent protein: implications for noninvasive imaging of transgene expression. Neoplasia, 1: 154-161, 1999; Wang, Y., Yu, Y., Shabahang, S., Wang, G., and Szalay, A. Renilla luciferase-Aequorea GFP (Ruc-GFP) fusion protein, a novel dual reporter for real-time imaging of gene expression in cell cultures and in live animals. Mol. Genet. Genomics, 268:160-168, 2002). These previous approaches have been limited by the inability to image single cells (Ray) or to take advantage of the low background signal with bioluminescence (Jacobs) or the advantage of tomographic imaging with PET (Wang). However, the ability to have a fluorescence, bioluminescence, and PET signal provides the full spectrum of coverage needed for many reporter gene applications. One can use this tri-fusion reporter gene to sort cells and to image in small living animals using either fluorescence or bioluminescence and in larger subjects, including humans, using PET. The ability to move between imaging technologies without having to use a different reporter gene for each application will greatly simplify various biological models including transgenics, cell trafficking, anticancer pharmaceutical research, and gene therapy.

Although our previous bi-fusion reporter construct ($tk_{20}rl$) showed well-correlated expression of PET and bioluminescence imaging modalities, it was somewhat limited by decreased TK activity and was susceptible to enzymatic cleavage into its component proteins. By changing the orientation of the fusion partner in the current vector, we could gain a significant amount of TK activity, indicating that the COOH-terminal end of thymidine kinase protein may be crucial for ensuring TK enzyme activity. In contrast, the hRL activity of the current construct showed a decrease in enzyme activity as opposed to our previous vector, which showed a gain in RL activity. However, this new synthetic version of Renilla luciferase (hRL) is 40-50-fold more active than original Renilla luciferase (Bhaumik, S., Lewis, X. Z., and Gambhir, S. S. Optical imaging of synthetic Renilla luciferase reporter gene expression in living mice. J. Biomed. Optics, in press, 2004), and therefore a drop in RL activity did not affect the efficacy of this vector significantly. Moreover, the tk gene in this triple fusion vector has a deletion of the first 135 bp that contains a nuclear localization signal and a cryptic testis-specific transcriptional start point (Degreve, B., Johansson, M., Declercq, E., Karlsson, A., and Balzarini, J. Differential intracellular compartmentalization of herpetic thymidine kinases (TKS) in TK genetransfected tumor cells. Molecular characterization of the nuclear localization signal of the herpes simplex virus type 1 TK. J. Virol., 72: 9535-9543, 1998; Cohen, J. L., Boyer, O., Salomon, B., Onclercq, R., Depetris, D., Lejeune, L., Dubus-Bonnet, V., Bruel, S., Charlotte, F., and Mattei, M. G. Fertile homozygous transgenic mice expressing a functional truncated herpes simplex thymidine kinase TK gene. Transgenic Res., 7: 321-330, 1998). Thus, this deletion leads to more cytoplasmic localization of TK enzyme, likely resulting in more TK activity (Luker, G. D., Sharma, V., Pica, C. M., Dahlheimer, J. L., Li, W., Ochesky, J., Ryan, C. E., Piwnica-Worms, H., and Piwnica-Worms, D. Noninvasive imaging of protein protein interactions in living animals. Proc. Natl. Acad. Sci. USA, 99: 6961-6966, 2002) due to the availability of greater amount of substrate (FHBG). This deletion mutant will also likely overcome the problem of male sterility in transgenic mice carrying the thymidine kinase gene due to production of a shorter transcript in testis from a cryptic transcriptional initiation site present in the first 135 bp of the gene. Another added advantage of this vector over our previous one and other vectors reported in the literature is that it can retain its integrity as a fusion protein when expressed, so that signal from each component of the tri-fusion protein will not be susceptible to problems related to cleavage. The absence of cleavage of the triple fusion vector is likely due to change of certain amino acids (Cys-Gly to Ser-Thr) present in the spacer in contrast to the previously reported 20-aa spacer of the tk20rl vector.

In the process of building a better multimodality vector, we constructed several other fusion vectors (see Table 1). Most of these vectors had lower ttK, luciferase, and RFP activity, probably due to the inherent nature of RFP (DsRed2) of forming obligate tetramer for proper maturation of the fluorophores present in the fusion genes. The tetrameric nature of RFP present in hrl/fl-rfrp-ttk fusions might impose structural and functional constrains on the other partner proteins resulting in decreased TK and luciferase activity. Our hrl/fl-egfpttk vectors did show a better TK and luciferase activity than hrl/fl-rfp-ttk vectors, due to the monomeric nature of eGFP proteins, but did not show better activity than the hrl/fl-mrfp-ttk fusion vectors. Moreover, the excitation and emission spectra of GFP ($\lambda_{ex}$, 489 nm; $\lambda_{em}$, 508 nm) is not as favorable for fluorescence imaging in living subjects as compared with RFP and mRFP because of the better penetration of red and near-infrared light in tissues. We also consistently observed a drop in tTK and RFP activity of the triple fusions with firefly luciferase in comparison with the fusions bearing Renilla luciferase. Fusion reporter vectors bearing truncated wild-type thymidine kinase also preserved a better wild-type thymidine kinase and luciferase activity (with both firefly and Renilla), and these vectors should be useful in the future when using other substrates (e.g., 2'-fluoro-5-fluoro-1-β-D-arbino-furanosyluracil/240 -deoxy-2'-fluoro-5-fluoro-1-β-D-arbinofuranosyluracil) that are more sensitive when used with wild-type thymidine kinase. It is likely that one tri-fusion will not serve the needs for all applications, and investigators will need to choose from a library of tri-fusions for a given application.

One of the potential uses of the multimodality reporter vectors in gene therapy is to target any type of cell line or tissues and then follow gene expression using a multimodality approach. Viral vectors, especially the lentiviral ones, are among the most standardized and widely used vectors to deliver any gene of interest to target tissues or an organism and to isolate cells, particularly nondividing cells stably expressing the gene. Recently, a bicistronic lentiviral vector carrying tk and fl reporter genes has been successfully used for PET and bioluminescence imaging in our laboratory (De, A., Lewis, X. H., and Gambhir, S. S. Noninvasive imaging of lentiviral-mediated reporter gene expression in living mice. Mol. Ther., 7: 681-691, 2003). The new lentiviral construct carrying the triple fusion gene described herein has been used successfully with FACS analysis to isolate lentiviral infected 293T and A375M cells stably expressing the triple fusion reporter. This lentiviral construct should have tremendous potential in wide variety of research applications. Our data with the A375M metastatic melanoma model further confirm the usefulness of this lentiviral vector carrying triple fusion reporter gene to follow progression of cancer metastases by molecular imaging. Extensions of this study with drug treatment are currently in progress (De, A., Collison, E., Kolodney, M., and Gambhir, S. Lentiviral reporter gene delivery as a novel way of studying therapeutic effects on cancer metastasis by noninvasive imaging. Mol. Ther., 7: S137, 2003).

Use of light is probably the oldest method of analyzing tissues in biomedical science. The various optical imaging approaches including fluorescence microscopy (at the cellular level), diffuse optical tomography, and intravital microscopy (for deeper structures at the organism level) are commonly used (Boas, D. A., Brooks, D. H., Miller, E. L., DiMarzio, C. A., Kilmer, M., Gaudette, R. J., and Zhang, Q. Imaging the body with diffuse optical tomography. IEEE Signal Processing Magazine, 18: 57-75, 2001; Jain, R. K., Munn, L. L., and Fukumura, D. Dissecting tumour pathophysiology using intravital microscopy. Nat. Rev. Cancer, 2: 266-276, 2002). However, intrinsic absorption and scattering of light through the tissues and autofluorescence properties of biological molecules (e.g., tryptophan, collagen, elastin, nicotineamide adenine dinucleotide, hemoglobin, oxyhemoglobin, and so forth) impose certain restrictions for using fluorescence as an imaging tool in small living subjects. However, both light attenuation and autofluorescence decline as wavelength increases, especially in the red to near-infrared region (>600 nm). A fluorescence protein/fluorochrome with excitation and emission toward red (560 nm onward) has better penetrability through the tissues than that with excitation and emission in the blue or green region. Moreover, hemoglobin and water, which are responsible for the highest absorption of light among all other biological molecules, have their lowest coefficient of absorption in the red and near-infrared region. Therefore, in vivo fluorescence imaging is more suitable in the red and near-infrared region than in the green or yellow region. Optical imaging in living subjects at the near-infrared region (650-900 nm) has therefore been used extensively by applying different fluorochromes that emit light at near-infrared region spectra and in combination with other imaging modalities (Ntziachristos, V., Bremer, C., and Weissleder, R. Fluorescence imaging with nearinfrared light: new technological advances that enable in vivo molecular imaging. Eur. Radiol., 13: 195-208, 2002; Zaheer, A., Lenkinsid, R. E., Mahmood, A., Jones, A. G., Cantley, L. C., and Frangioni, J. V. In vivo near-infrared fluorescence imaging of osteoblastic activity. Nat. Biotechnol., 19: 1148-1154, 2001). However, synthesis and attachment of these fluorochromes to proteins/copolymers require complex chemical procedures and are more difficult to generalize. Also, these strategies are not directly applicable to genetically encoded reporters. The mRFP1 protein used in this study has an excitation and emission range in the far-red region (584-607 nm) and thus is one of the better reporter gene choices for fluorescence imaging in living subjects (Campbell, R. E., Tour, O., Palmer, A. E., Steinbach, P. A., Geoffrey, S., Baird, G. S., David, A. Z., and Tsien, R. Y. A monomeric red fluorescent protein. Proc. Natl. Acad. Sci. USA, 99: 7877-7882, 2002). The monomeric nature of this protein also confers a better functional preservation as fusion partner as compared with RFP or DsRed2 (tetramer) and HcRed (dimer). However, we still observed a significant amount of autofluorescence from the mouse relative to bioluminescence, which is not limited by autofluorescence, and therefore bioluminescence produced a better signal:background ratio in living animals. However, bioluminescence imaging of gene expression in a single cell is not easily possible due to generation of relatively low amounts of light. Therefore, the current results would support using the fluorescence component for cell imaging/sorting with limited in vivo imaging, bioluminescence for small animal imaging even with a very few number of cells, and PET for tomographically imaging living subjects including larger animals and humans.

Our cancer metastatic model shows that metastases can be imaged by microPET and bioluminescence in living mice using this triple fusion reporter gene, with certain limitations for each technique. The bioluminescence signal from Renilla luciferase is not detectable from metastases present at greater depths but is easily detectable from superficial metastases from any region of the body. On the other hand, microPET reveals metastases from deep inside the body, but signals from metastases in the abdomen/pelvis are somewhat obscured by the nonspecific signal in the gastrointestinal tract and urinary collecting system due to tracer clearance. Finally, autofluorescing properties of biological molecules limit detection of metastases by in vivo fluorescence imaging in living animals. However, metastases can be easily visualized in sacrificed animals with exposed tissues in situ using whole body fluorescence imaging. It is likely that the fluorescence signal to background can be improved by using an excitation source under the animal and imaging with a camera above the animal to help minimize autofluorescence. The bioluminescence signal can also be markedly improved by injecting higher doses of substrate (coelenterazine), as we have demonstrated recently (Bhaumik, S., Lewis, X. Z., and Gambhir, S. S. Optical imaging of synthetic Renilla luciferase reporter gene expression in living mice. J. Biomed. Optics, in press, 2004). As red-shifted bioluminescent reporters with high substrate utilization capacity are developed, this will also likely aid in helping to use bioluminescence-based reporter fusions. In addition, the microPET signal can be improved by using tracers with longer half-lives (e.g., $^{124}$I-labeled 2'-fluoro-5-fluoro-1-β-D-arbinofuranosyluracil) to allow the background signal from the gastrointestinal tract and renal collecting system to be reduced by waiting longer after tracer injection before imaging animals. With continued refinement in reporter genes, substrates for reporter proteins, and physical instrumentation, it is likely that higher spatial resolution imaging with greater sensitivity for detecting smaller numbers of cells will eventually be possible.

Additional studies quantitatively comparing fluorescence, bioluminescence, and PET in small living animals should also help to better define the potential roles of each modality in specific applications. Cancer research, including imaging of preclinical models of tumors and metastases, immune cell trafficking, transgenic models, gene therapy, and monitoring therapy in general should all benefit from the strategies described herein.

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention.

In particular, it is to be understood that this invention is directed to any fusion vector coupling any fluorescent protein (including, but not limited to, green, yellow and red fluorescent protein) and any bioluminescent protein (including, but not limited to, Renilla Luciferase and Firefly Luciferase) with any PET reporter gene (including, but not limited to, HSV1-sr39tk). It should also be appreciated that these reporter genes may be arranged in any order in the fusion vector, relative to each other.

Moreover, this invention is not limited to the particular methodology, protocols, cell lines, animal species or genera, constructs, and reagents described as such may vary, as will be appreciated by one of skill in the art. The scope of the invention is, therefore, indicated by the following claims rather than by the foregoing description. All changes, modifications, and variations coming within the meaning and range of equivalency of the claims are to be considered within their scope.

We claim:

1. A triple fusion nucleic acid expression vector, comprising:
   a first reporter nucleic acid sequence, a second reporter nucleic acid sequence, a third reporter nucleic acid sequence, a first nucleic acid linker sequence, and a second nucleic acid linker sequence, wherein:
   (i) the first reporter nucleic acid sequence, the second reporter nucleic acid sequence, the third reporter nucleic acid sequence, the first nucleic acid linker sequence, and the second nucleic acid linker sequence are operably linked to an expression control system and co-expressible as a single fusion polypeptide therefrom;
   (ii) the first reporter nucleic acid sequence and the second reporter nucleic acid sequence are separated from each ether by the first nucleic acid linker sequence;
   (iii) the second reporter nucleic acid sequence and the third reporter nucleic acid sequence are separated from each other by the second nucleic acid linker sequence;
   (iii) each of the first, second, and third reporter nucleic acid sequences encodes an individual imageable reporter region of the expressed fusion polypeptide;
   (iv) each of the individual imageable reporter regions of the fusion polypeptide is imageable by a method selected from the group consisting of: detecting bioluminescence, detecting fluorescence, and positron emission topography, wherein no two reporter regions are imageable by the same method; and (v) the first nucleic acid linker sequence encodes a first polypeptide linker having the amino acid sequence SEQ ID NO: 9, and the second nucleic acid linker sequence encodes a second polypeptide linker having the amino acid sequence SEQ ID NO: 10.

2. The triple fusion expression vector of claim 1, wherein the nucleic acid sequence encoding the imageable reporter region of the fusion polypeptide that is imageable by positron emission topography encodes herpes simplex virus type 1 sr39 thymidine kinase (HSVl-sr39 thymidine kinase).

3. The triple fusion expression vector of claim 1, wherein the first nucleic acid encodes wild type HSVl thymidine kinase.

4. The triple fusion expression vector of claim 1, wherein the first nucleic acid encodes a bioluminescent polypeptide.

5. The triple fusion expression vector of claim 4, wherein the first nucleic acid encodes renilla luciferase.

6. The triple fusion expression vector of claim 4, wherein the first nucleic acid encodes firefly luciferase.

7. The triple fusion expression vector of claim 1, wherein the first nucleic acid encodes a fluorescence polypeptide.

8. The triple fusion expression vector of claim 7, wherein the first nucleic acid encodes red fluorescence protein.

9. The triple fusion expression vector of claim 7, wherein the first nucleic acid encodes green fluorescence protein.

10. A cultured cell comprising the vector of claim 1.

11. A cultured cell transfected with the vector of claim 1, or a progeny of said cell, wherein the cell expresses the triple fusion polypeptide.

12. An isolated non-human cell comprising the vector of claim 1.

13. An isolated non-human cell transfected with the vector of claim 1, or a progeny of said cell, wherein the cell expresses the triple fusion polypeptide.

14. A cultured cell comprising:

a first reporter nucleic acid sequence encoding a polypeptide region imageable by positron emission topography; a second reporter nucleic acid sequence encoding a bioluminescent polypeptide; a third reporter nucleic acid sequence encoding a fluorescent polypeptide; a first nucleic acid linker sequence, and a second nucleic acid linker sequence, wherein:

(i) the first reporter nucleic acid sequence, the second reporter nucleic acid sequence, the third reporter nucleic acid sequence, the first nucleic acid linker sequence, and the second nucleic acid linker sequence are operably linked to an expression control system and co-expressible as a single fusion polypeptide therefrom, and wherein the order of transcription from the expression control system is the first nucleic acid sequence, the second nucleic acid sequence, and the third nucleic acid sequence;

(ii) the first reporter nucleic acid sequence and the second reporter nucleic acid sequence are separated from each other by the first nucleic acid linker sequence;

(iii) the second reporter nucleic acid sequence and the third reporter nucleic acid sequence are separated from each other by the second nucleic acid linker sequence;

(iv) each of the first, second, and third reporter nucleic acid sequences encodes an individual imaqeable reporter region of the expressed fusion polypeptide; and (v) the first nucleic acid linker sequence encodes a first polypeptide linker having the amino acid sequence SEQ ID NO: 9, and the second nucleic acid linker sequence encodes a second polypeptide linker having the amino acid sequence SEQ ID NO: 10.

15. An isolated non-human cell comprising:

a first reporter nucleic acid sequence encoding a polypeptide region imageable by positron emission topography; a second reporter nucleic acid sequence encoding a bioluminescent polypeptide; a third reporter nucleic acid sequence encoding a fluorescent polypeptide; a first nucleic acid linker sequence, and a second nucleic acid linker sequence, wherein:

(i) the first reporter nucleic acid sequence, the second reporter nucleic acid sequence, the third reporter nucleic acid sequence, the first nucleic acid linker sequence, and the second nucleic acid linker sequence are operably linked to an expression control system and co-expressible as a single fusion polypeptide therefrom, and wherein the order of transcription from the expression control system is the first nucleic acid sequence, the second nucleic acid sequence, and the third nucleic acid sequence;

(ii) the first reporter nucleic acid sequence and the second reporter nucleic acid sequence are separated from each other by the first nucleic acid linker sequence;

(iii) the second reporter nucleic acid sequence and the third reporter nucleic acid sequence are separated from each other by the second nucleic acid linker sequence;

(iv) each of the first, second, and third reporter nucleic acid sequences encodes an individual imaqeable reporter region of the expressed fusion polypeptide; and (v) the first nucleic acid linker sequence encodes a first polypeptide linker having the amino acid sequence SEQ ID NO: 9, and the second nucleic acid linker sequence encodes a second polypeptide linker having the amino acid sequence SEQ ID NO: 10.

16. A triple fusion expression vector comprising:

a first reporter nucleic acid sequence, wherein the first reporter nucleic acid sequence encodes a synthetic renilla luciferase;

a second reporter nucleic acid sequence, wherein the second reporter nucleic acid sequence encodes a red fluorescence protein;

a third reporter nucleic acid sequence, wherein the third reporter nucleic acid encodes a HSV1-sr39 thymidine kinase; and two nucleic acid linker sequences, wherein:

(i) the first reporter nucleic acid sequence, the second reporter nucleic acid sequence, the third reporter nucleic acid sequence, the first nucleic acid linker sequence, and the second nucleic acid linker sequence are operably linked to an expression control system and co-expressible as a single fusion polypeptide therefrom, and wherein the order of transcription from the expression control system is the first nucleic acid sequence, the second nucleic acid sequence, and the third nucleic acid sequence;

(ii) the first reporter nucleic acid sequence and the second reporter nucleic acid sequence are separated from each other by the first nucleic acid linker sequence; and (iii) the second reporter nucleic acid sequence and the third reporter nucleic acid sequence are separated from each other by the second nucleic acid linker sequence; and
(v) the first nucleic acid linker sequence encodes a first polypeptide linker having the amino acid sequence SEQ ID NO: 9, and the second nucleic acid linker sequence encodes a second polypeptide linker having the amino acid sequence SEQ ID NO: 10.

* * * * *

SEQUENCE LISTING

```
<160> NUMBER OF SEQ ID NOS: 10

<210> SEQ ID NO 1
<211> LENGTH: 25
<212> TYPE: PRT
<213> ORGANISM: Artificial Sequence
<220> FEATURE:
<223> OTHER INFORMATION: Primer Sequence
```

-continued

```
<400> SEQUENCE: 1

Gly Ala Gly Cys Cys Thr Cys Gly Ala Gly Thr Thr Ala Gly Cys
1               5                   10                  15

Cys Thr Cys Cys Cys Cys Cys Ala Thr
            20                  25

<210> SEQ ID NO 2
<211> LENGTH: 25
<212> TYPE: PRT
<213> ORGANISM: Artificial Sequence
<220> FEATURE:
<223> OTHER INFORMATION: Primer Sequence

<400> SEQUENCE: 2

Gly Ala Gly Cys Gly Ala Ala Thr Thr Cys Gly Thr Thr Ala Gly Cys
1               5                   10                  15

Cys Thr Cys Cys Cys Cys Cys Ala Thr
            20                  25

<210> SEQ ID NO 3
<211> LENGTH: 25
<212> TYPE: PRT
<213> ORGANISM: Artificial Sequence
<220> FEATURE:
<223> OTHER INFORMATION: Primer Sequence

<400> SEQUENCE: 3

Gly Ala Gly Cys Ala Ala Gly Cys Thr Thr Gly Thr Thr Ala Gly Cys
1               5                   10                  15

Cys Thr Cys Cys Cys Cys Cys Ala Thr
            20                  25

<210> SEQ ID NO 4
<211> LENGTH: 31
<212> TYPE: PRT
<213> ORGANISM: Artificial Sequence
<220> FEATURE:
<223> OTHER INFORMATION: Primer Sequence

<400> SEQUENCE: 4

Gly Cys Ala Gly Cys Thr Ala Gly Cys Cys Gly Cys Cys Ala Cys Cys
1               5                   10                  15

Ala Thr Gly Gly Cys Thr Thr Cys Gly Thr Ala Cys Cys Cys Cys
            20                  25                  30

<210> SEQ ID NO 5
<211> LENGTH: 20
<212> TYPE: PRT
<213> ORGANISM: Artificial Sequence
<220> FEATURE:
<223> OTHER INFORMATION: Spacer Sequence

<400> SEQUENCE: 5

Asn Ser His Ala Ser Ala Gly Tyr Gln Ala Cys Gly Thr Ala Gly Pro
1               5                   10                  15

Gly Ser Thr Gly
            20

<210> SEQ ID NO 6
<211> LENGTH: 18
<212> TYPE: PRT
<213> ORGANISM: Artificial Sequence
<220> FEATURE:
<223> OTHER INFORMATION: Spacer Sequence
```

-continued

```
<400> SEQUENCE: 6

Ser Arg Val Cys Arg Leu Ser Ser Leu Arg Tyr Arg Gly Pro Gly Ile
1               5                   10                  15

Thr Gly

<210> SEQ ID NO 7
<211> LENGTH: 10
<212> TYPE: PRT
<213> ORGANISM: Artificial Sequence
<220> FEATURE:
<223> OTHER INFORMATION: Spacer Sequence

<400> SEQUENCE: 7

Ala Val Pro Arg Ala Arg Asp Pro Thr Gly
1               5                   10

<210> SEQ ID NO 8
<211> LENGTH: 22
<212> TYPE: PRT
<213> ORGANISM: Artificial Sequence
<220> FEATURE:
<223> OTHER INFORMATION: Spacer Sequence

<400> SEQUENCE: 8

Leu Glu Asn Ser His Ala Ser Ala Gly Tyr Gln Ala Cys Gly Thr Ala
1               5                   10                  15

Gly Pro Gly Ser Thr Gly
            20

<210> SEQ ID NO 9
<211> LENGTH: 14
<212> TYPE: PRT
<213> ORGANISM: Artificial Sequence
<220> FEATURE:
<223> OTHER INFORMATION: Spacer Sequence

<400> SEQUENCE: 9

Leu Glu Asn Ser His Ala Ser Ala Gly Tyr Gln Ala Ser Thr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Spacer Sequence

<400> SEQUENCE: 10

Thr Ala Gly Pro Gly Ser Ala Thr
1               5
```